United States Patent
Massadeh et al.

(10) Patent No.: US 10,709,795 B2
(45) Date of Patent: *Jul. 14, 2020

(54) METHOD FOR DELIVERING PHARMACEUTICAL NANOPARTICLES TO CANCER CELLS

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Salam Massadeh, Riyadh (SA); Manal Alaamery, Riyadh (SA)

(73) Assignees: National Guard Health Affairs, Riyadh (NR); King Saud bin Abdulaziz University for Health Sciences, Riyadh (SA); King Abdullah International Medical Research Center, Riyadh (SA)

(*) Notice: Subject to any disclaimer, the term of this patent is extended or adjusted under 35 U.S.C. 154(b) by 0 days.

This patent is subject to a terminal disclaimer.

(21) Appl. No.: 16/412,047

(22) Filed: May 14, 2019

(65) Prior Publication Data

US 2019/0298856 A1 Oct. 3, 2019

Related U.S. Application Data

(63) Continuation of application No. 15/480,817, filed on Apr. 6, 2017, now Pat. No. 10,369,230.

(51) Int. Cl.
| | | |
|---|---|---|
| *A61K 47/69* | (2017.01) | |
| *A61K 47/68* | (2017.01) | |
| *C07K 16/32* | (2006.01) | |
| *A61K 31/4196* | (2006.01) | |
| *A61K 9/51* | (2006.01) | |

(52) U.S. Cl.
CPC ...... *A61K 47/6935* (2017.08); *A61K 31/4196* (2013.01); *A61K 47/68* (2017.08); *A61K 47/6937* (2017.08); *C07K 16/32* (2013.01); *A61K 9/5146* (2013.01); *A61K 9/5153* (2013.01)

(58) Field of Classification Search
CPC ............... A61K 31/4196; A61K 47/68; A61K 47/6935; A61K 47/6937; A61K 9/5146; A61K 9/5153; C07K 16/32
See application file for complete search history.

(56) References Cited

U.S. PATENT DOCUMENTS

| | | | |
|---|---|---|---|
| 8,420,123 B2 | 4/2013 | Troiano et al. | |
| 10,369,230 B2* | 8/2019 | Massadeh | A61K 47/6937 |
| 2009/0061010 A1 | 3/2009 | Zale et al. | |
| 2013/0101672 A1* | 4/2013 | Cheng | A61K 9/0019 |
| | | | 424/491 |
| 2014/0004185 A1 | 1/2014 | Chirwa | |
| 2015/0258102 A1 | 9/2015 | Bagrodia et al. | |
| 2016/0235860 A1 | 8/2016 | Markovic et al. | |

FOREIGN PATENT DOCUMENTS

| | | |
|---|---|---|
| WO | WO 2012/054923 A2 | 4/2012 |
| WO | WO 2016/004290 A1 | 1/2016 |
| WO | WO 2016/131006 A1 | 8/2016 |
| WO | WO 2017/031084 | 2/2017 |

OTHER PUBLICATIONS

Salam Massadeh, et al., "Synthesis of protein-coated biocompatible methotrexate-loaded PLA-PEG-PLA nanoparticles for breast cancer treatment", Nano Reviews and Experiments, vol. 7, Jun. 16, 2016, 10 pages.

Hai Wang, et al., "Enhanced anti-tumor efficacy by co-delivery of doxorubicin and paclitaxel with amphiphilic methoxy PEG-PLGA copolymer nanoparticles", Biomaterials, vol. 32, 2011, pp. 8281-8290.

C.E. Mora-Huertas, et al., "Polymer-based nanocapsules for drug delivery", International Journal of Pharmaceutics, vol. 385, 2010, pp. 113-142.

* cited by examiner

*Primary Examiner* — Anna R Falkowitz
(74) *Attorney, Agent, or Firm* — Oblon, McClelland, Maier & Neustadt, L.L.P.

(57) ABSTRACT

A nanoparticle that has a membrane including a polylactide-block-poly(ethylene glycol)-block-polylactide (PLA-PEG-PLA) and a polyvinyl alcohol, a bovine serum albumin contacting the membrane on the outside of the nanoparticle, a targeting group attached to the outside of the nanoparticle, and a breast cancer therapeutic agent that is encapsulated by the membrane. A nanoparticle that consists of a membrane including a polylactide-block-poly(ethylene glycol)-block-polylactide (PLA-PEG-PLA) and a polyvinyl alcohol, a bovine serum albumin contacting the membrane on the outside of the nanoparticle, breast cancer therapeutic agent that is encapsulated by the membrane, and an anti-Her2 antibody attached to the outer surface of the nanoparticle. A range of a number average molecular weight of the PEG block is 800 Da to 3 kDa and a range of a number average molecular weight of each of the PLA blocks is from 1 kDa to 5 kDa.

19 Claims, 22 Drawing Sheets

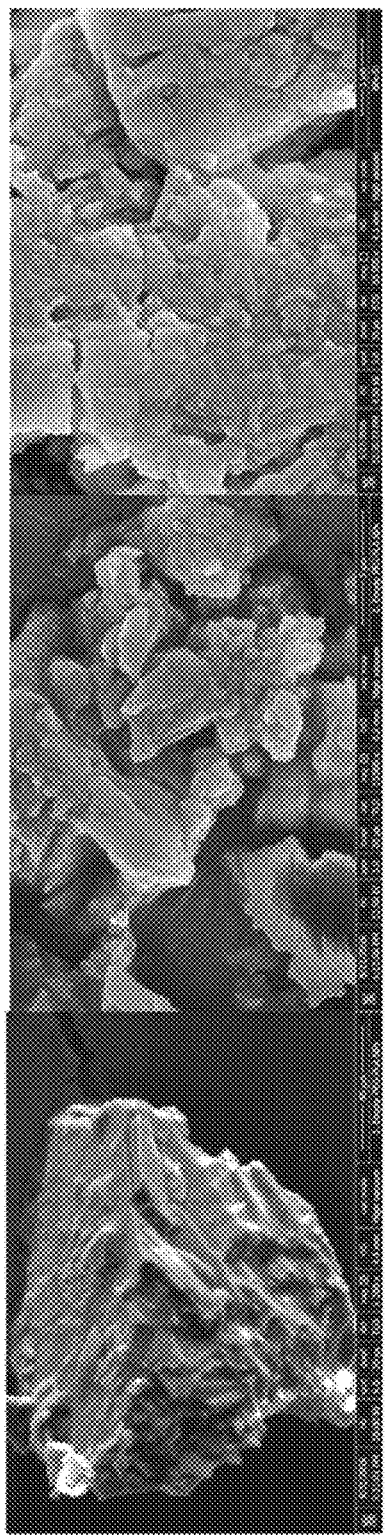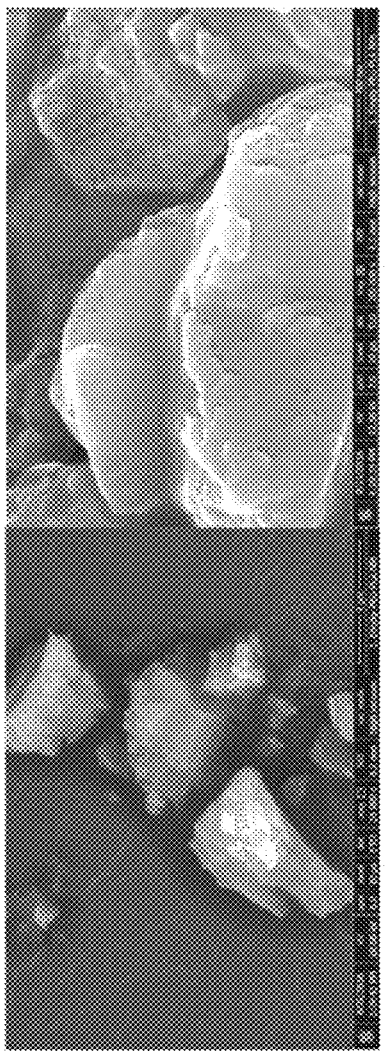
FIG. 4A  FIG. 5A  FIG. 6
FIG. 4B  FIG. 5B

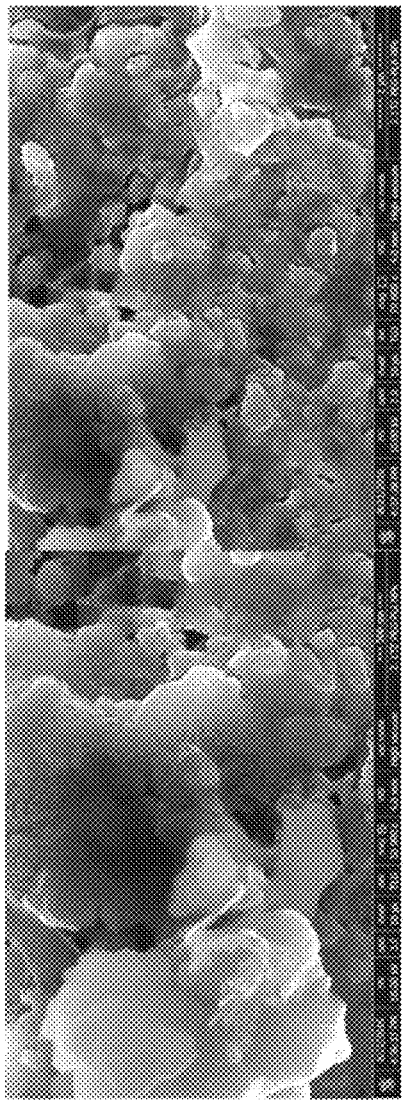
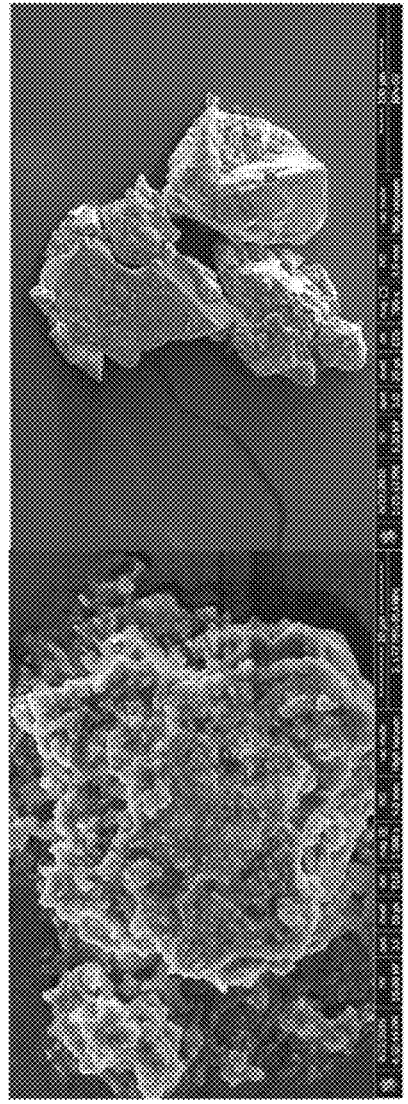
FIG. 9A
FIG. 9B
FIG. 9C
FIG. 10

METHOD FOR DELIVERING PHARMACEUTICAL NANOPARTICLES TO CANCER CELLS

CROSS-REFERENCE TO RELATED APPLICATIONS

The present application is a Continuation of Ser. No. 15/480,817, now allowed, having a filing date of Apr. 6, 2017.

BACKGROUND OF THE INVENTION

Technical Field

The present invention relates to a targeted sustained release PLA-PEG-PLA nanoparticle loaded with a breast cancer therapeutic agent.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Systems that deliver drugs to a patient (e.g., targeted to a particular tissue or cell type or targeted to a specific diseased tissue but not normal tissue), or that control release of drugs has long been recognized as beneficial. For example, therapeutics that include an active drug and that are capable of locating in a particular tissue or cell type e.g., a specific diseased tissue, may reduce the amount of the drug in tissues of the body that do not require treatment. This is particularly important when treating a condition such as cancer where it is desirable that a cytotoxic dose of the drug is delivered to cancer cells without killing the surrounding non-cancerous tissue. Further, such therapeutics may reduce the undesirable and sometimes life threatening side effects common in anticancer therapy. For example, nanoparticle therapeutics may, due to the small size, evade recognition within the body allowing for targeted and controlled delivery while e.g., remaining stable for an effective amount of time.

Therapeutics that offer such therapy and/or controlled release and/or targeted therapy also must be able to deliver an effective amount of drug. It can be a challenge to prepare nanoparticle systems that have an appropriate amount of drug associated each nanoparticle, while keeping the size of the nanoparticles small enough to have advantageous delivery properties. For example, while it is desirable to load a nanoparticle with a high quantity of therapeutic agent, nanoparticle preparations that use a drug load that is too high will result in nanoparticles that are too large for practical therapeutic use. Further, it may be desirable for therapeutic nanoparticles to remain stable so as to e.g. substantially limit rapid or immediate release of the therapeutic agent. Sustained release therapeutics may offer reduced costs in drug dosing to the patient.

Letrozole is a water insoluble chemotherapeutic agent; it is a first line anti-breast cancer drug. Letrozole is an FDA approved drug for the treatment of local or metastatic breast cancer that is hormone receptor positive or has an unknown receptor status in postmenopausal women. It is marketed as Femara. The available dosage form currently given is highly concentrated (2.5 mg/tablet), and it causes many adverse effects like high cholesterol, bone effects, hepatic impairment, and other reported adverse effects. All of these adverse effects are caused by nonspecific interactions with non-target tissue (Table 1).

TABLE 1

Occurrence of adverse side effects as a result of Femara.

| Adverse Reaction | Grades 1-4 Femara N = 2448 n (%) | | Grades 3-4 Femara N = 2448 n (%) | |
|---|---|---|---|---|
| Pts with any adverse event | 2310 | 94.4 | 635 | 25.9 |
| Hypercholesterolemia | 1280 | 52.3 | 11 | 0.4 |
| Hot Flashes/Flushes | 821 | 33.5 | 0 | — |
| Arthralgia/Arthritis | 618 | 25.2 | 85 | 3.5 |
| Night Sweats | 357 | 25.2 | 0 | — |
| Bone Fractures | 338 | 14.6 | — | — |
| Weight Increase | 317 | 13.8 | 27 | 1.1 |
| Nausea | 283 | 11.6 | 6 | 0.2 |
| Bone Fractures | 247 | 10.1 | — | — |
| Fatigue (Lethargy, Malaise, Asthenia) | 235 | 9.6 | 6 | 0.2 |
| Myalgia | 217 | 8.9 | 18 | 0.7 |
| Edema | 164 | 6.7 | 3 | 0.1 |
| Weight Decrease | 140 | 5.7 | 8 | 0.3 |
| Vaginal Bleeding | 128 | 5.2 | 1 | <0.1 |
| Back pain | 125 | 5.1 | 7 | 0.3 |
| Osteoporosis NOS | 124 | 5.1 | 10 | 0.4 |
| Bone Pain | 123 | 5.0 | 6 | 0.2 |
| Depression | 119 | 4.9 | 16 | 0.7 |
| Vaginal Irritation | 111 | 4.5 | 2 | <0.1 |
| Headache | 105 | 4.3 | 9 | 0.4 |
| Pain in extremity | 103 | 4.2 | 6 | 0.1 |
| Osteopenia | 87 | 3.6 | 0 | — |
| Dizziness/Light headedness | 84 | 3.4 | 1 | <0.1 |
| Alopecia | 83 | 3.4 | 0 | — |
| Vomiting | 80 | 3.3 | 3 | 0.1 |
| Cataract | 49 | 2.0 | 16 | 0.7 |
| Constipation | 49 | 2.0 | 3 | 0.1 |
| Breast Pain | 37 | 2.0 | 1 | <0.1 |
| Anorexia | 20 | 1.5 | 1 | <0.1 |
| Endometrial Hyperplasia/Cancer | 11/1909 | 0.8 | — | — |
| Endometrial proliferation Disorders | 10 | 0.3 | 0 | — |
| Endometrial Hyperplasia/Cancer | 6/1909 | 0.3 | — | — |
| Other Endometrial Disorders | 2 | <0.1 | 0 | — |
| Myocardial Infarction | 24 | 1.0 | — | — |
| Myocardial Infarction | 37 | 1.5 | — | — |
| Myocardial Ischemia | 6 | 0.2 | — | — |
| Cerebrovascular Accident | 52 | 2.1 | — | — |
| Cerebrovascular Accident | 70 | 2.9 | — | — |
| Angine | 26 | 1.1 | — | — |
| Angina | 32 | 1.3 | — | — |
| Thromboembolic Event | 51 | 2.1 | — | — |
| Thromboembolic Event | 71 | 2.9 | — | — |
| Other Cardiovascular1 | 260 | 10.6 | — | — |
| Other Cardiovascular1 | 312 | 12.7 | — | — |
| Second Malignancies | 53 | 2.2 | — | — |
| Second Malignancies | 102 | 4.2 | — | — |

In view of the forgoing, one objective of the present disclosure is to provide a nanoparticle with sustained release and targeting properties for a cancer therapeutic.

BRIEF SUMMARY OF THE INVENTION

According to a first aspect, the present disclosure relates to a nanoparticle having a membrane comprising a polylactide-block-poly(ethylene glycol)-block-polylactide (PLA-PEG-PLA) copolymer and a polyvinyl alcohol polymer, a bovine serum albumin contacting the membrane on the outer surface of the membrane, a cancer targeting agent attached to the outer surface of the membrane, and a breast cancer therapeutic agent that is encapsulated by the membrane. PLA-PEG-PLA has a number average molecular weight range of the PEG block of 800 Da to 3 kDa and a number average molecular weight range of each of the PLA blocks of 1 kDa to 5 kDa. The nanoparticles are biocompatible and may be useful for treating breast cancer. These nanoparticles may also offer sustained release of the breast cancer therapeutic agent.

In some embodiments, the polyvinyl alcohol is a weight average molecular weight from 85 kDa to 100 kDa.

In some embodiments, the polylactide-block-poly(ethylene glycol)-block-polylactide (PLA-PEG-PLA) is 60 to 95 weight percent relative to the total weight of the nanoparticle, and 0.5 to 5 weight percent of polyvinyl alcohol relative to the total weight of the nanoparticle.

In some embodiments, the bovine serum albumin is 0.5 to 8 weight percent relative to the total weight of the nanoparticle.

In some embodiments, the nanoparticle has a diameter of 300 nm to 370 nm.

In some embodiments, a rate of release of the breast cancer therapeutic agent is a cumulative percent of 25% to 75% in 24 hours to 96 hours.

In some embodiments, the cancer targeting agent is an anti-Her2 antibody.

In some embodiments, the anti-Her2 antibody is sourced from a rabbit.

In some embodiments, the nanoparticle has a diameter of 310 nm to 350 nm.

In some embodiments, the anti-Her2 antibody is conjugated to the membrane.

In some embodiments, the breast cancer therapeutic agent is at least one selected from the group consisting of letrozole, cetuximab, gleevac, idarubicin, trastuzumab, lapatinib, paclitaxel, and a salt thereof.

In some embodiments, the breast cancer therapeutic agent is 0.5 to 10 weight percent relative to the weight of the nanoparticle.

In some embodiments, the nanoparticle has an internal volume of 1 picoliter to 1 nanoliter.

In some embodiments, the nanoparticle has a zeta potential of −7 mV to −20 mV.

In some embodiments, the membrane further includes a diblock copolymer.

In some embodiments, a weight percent of the diblock copolymer relative to the nanoparticle is 0.01% to 0.1%.

In some embodiments, the diblock copolymer has one hydrophobic polymer block and one hydrophilic polymer block.

In some embodiments, the diblock copolymer has at least one hydrophobic polymer block selected from the group consisting of polycaprolactone (PCL), polyvalerolactone (PVL), poly(lactide-co-glycolide) (PLGA), polylactic acid (PLA), polybutyrolactone (PBL), polyglycolide, or polypropiolactone (PPL), and one hydrophilic polymer block selected from the group consisting of polyethylene glycol (PEG), hyaluronic acid (HA), or poly-γ-glutamic acid (PGA).

In some embodiments, a range of number average molecular weight range of the hydrophobic block and the hydrophilic block is from 800 Da to 5 kDa.

In one embodiment, the membrane is prepared by a double emulsion method comprising mixing a first emulsion with a second emulsion, where the first emulsion and the second emulsion comprise polyvinyl alcohol as an emulsifying agent.

In one embodiment, the nanoparticle consists of a membrane comprising a polylactide-block-poly(ethylene glycol)-block-polylactide (PLA-PEG-PLA) and a polyvinyl alcohol, a bovine serum albumin contacting the membrane on the outside of the nanoparticle, a breast cancer therapeutic agent that is encapsulated by the membrane, and an anti-Her2 antibody attached to an outer surface of the membrane. A range of a number average molecular weight of the PEG block is 800 Da to 3 kDa and a range of a number average molecular weight of each of the PLA blocks is from 1 kDa to 5 kDa.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 4A is a scanning electron micrograph of an embodiment of crystallized nanoparticles prior to incorporating the breast cancer therapeutic agent into the interior space at 1,200× magnification;

FIG. 4B is a scanning electron micrograph of an embodiment of crystallized nanoparticles prior to incorporating the breast cancer therapeutic agent into the interior space at 24,000× magnification;

FIG. 5A is a scanning electron micrograph of crystallized nanoparticles prior to incorporating the breast cancer therapeutic agent into the interior space at 15,000× magnification;

FIG. 5B is a scanning electron micrograph of crystallized nanoparticles prior to incorporating the breast cancer therapeutic agent into the interior space at 100,000× magnification;

FIG. 6 is a scanning electron micrograph of an embodiment of crystallized nanoparticles after incorporating the breast cancer therapeutic agent into the interior space at 65,000× magnification;

FIG. 9A is a scanning electron micrograph of an embodiment of crystallized complete nanoparticles at 50,000× magnification;

FIG. 9B is a scanning electron micrograph of an embodiment of crystallized complete nanoparticles at 5,000× magnification;

FIG. 9C is a scanning electron micrograph of an embodiment of crystallized complete nanoparticles at 70,000× magnification;

FIG. 10 is a scanning electron micrograph of an embodiment of crystallized nanoparticles after incorporating the breast cancer therapeutic agent into the interior space at a 700× magnification;

DETAILED DESCRIPTION OF THE EMBODIMENTS

Figure 1A:
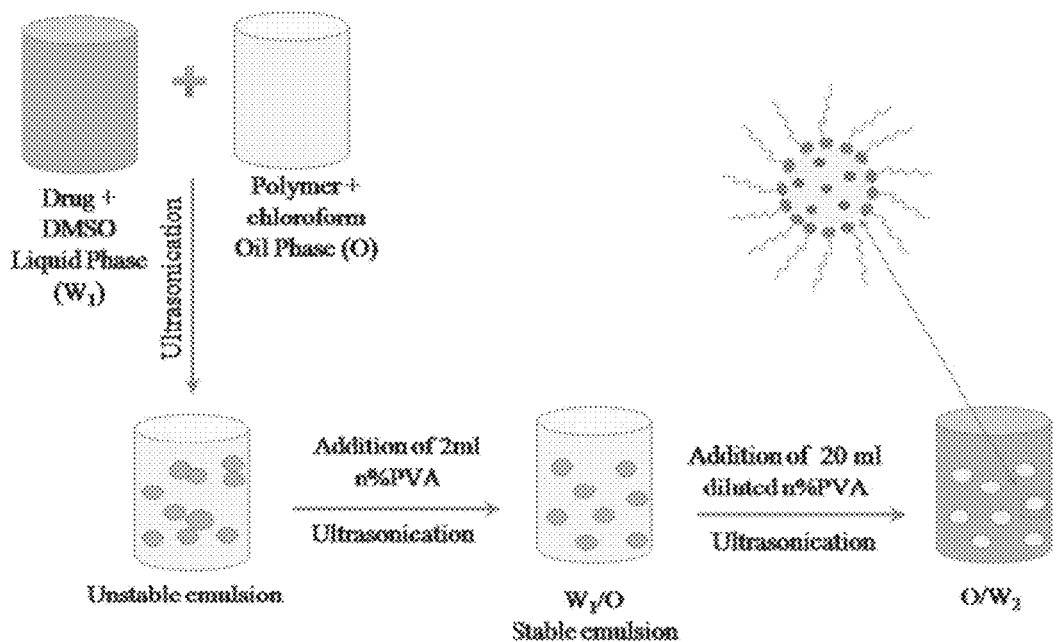
FIG. 1A is a schematic of a method of filling the nanoparticles with the breast cancer therapeutic.

The present disclosure relates to a nanoparticle having a membrane comprising a polylactide-block-poly(ethylene glycol)-block-polylactide block (PLA-PEG-PLA) copolymer and a polyvinyl alcohol polymer, a bovine serum albumin contacting an outer surface of the membrane (i.e. contacting the outside surface of the nanoparticle), a cancer targeting agent contacting the outer surface of the membrane, and a breast cancer therapeutic agent that is encapsulated by the membrane.

The PLA-PEG-PLA polymer is a triblock copolymer. Block copolymers are made up of different polymerized monomers covalently bonded in segments. In the PLA-PEG-PLA polymer, there are three blocks, a first PLA block, a PEG block, and a second PLA block, which together make a triblock copolymer. The PLA-PEG-PLA copolymer of the present disclosure may have a number average molecular weight range of the PEG block of from 800 Da to 3 kDa, from 1.5 kDa to 2.5 kDa, or from 1.75 kDa to 2.25 kDa. A number average molecular weight range of the first PLA block is in a range of from 1 kDa to 5 kDa, from 1.5 kDa to 4.5 kDa, from 2 kDa to 4 kDa, from 2.5 kDa to 3.5 kDa, or from 2.75 kDa to 3.25 kDa. A number average molecular weight range of the second PLA block is a range of from 1 kDa to 5 kDa, from 1.5 kDa to 4.5 kDa, from 2 kDa to 4 kDa, from 2.5 kDa to 3.5 kDa, or from 2.75 kDa to 3.25 kDa. The first PLA block and the second PLA block may have different number average molecular weights relative to each other.

The PLA blocks of the copolymer are hydrophobic, and the PEG block is hydrophilic. The membrane of the nanoparticle comprises the copolymer. Spherical structures formed by the PLA-PEG-PLA copolymer, which may be referred to as polymersomes, have an interior space, and interior surface, an intermembrane space, and an exterior surface. The polymersome is a hollow spherical shape having synthetic polymers that encircle the circumference of the spherical shape. In the polymersome, the hollow center is the interior space of the polymersome. The membrane enclosing the sphere has an exterior facing portion, the exterior surface of the polymersome, and an interior facing portion, the interior surface of the polymersome. The span between the exterior surface and the interior surface of the polymersome is the intermembrane space. The polymersome formed may tend to have a hydrophobic exterior surface and interior membrane, whereas an intermembrane space, formed by the PEG block, will be hydrophilic. In some embodiments, the PLA-PEG-PLA copolymer is 60 to 95 weight percent or 70 to 85 weight percent, relative to the total weight of the nanoparticle. In some embodiments, a membrane thickness, or a span of the intermembrane space may be from 120 nm to 2 microns, from 250 nm to 1.75 microns, from 0.5 microns to 1.5 microns, from 0.75 microns to 1.25 microns, or from 1 micron to 1.1 microns.

In some embodiments of the nanoparticle, the membrane may further include a diblock copolymer (i.e. two blocks of polymers). In some embodiments, a weight percent of the diblock copolymer relative to the total weight of the nanoparticle is 0.01% to 0.1%, 0.05% to 0.08%, or 0.06% to 0.07%. In some embodiments, the diblock copolymer has one hydrophobic block and one hydrophilic block. In some embodiments, the ratio of the number average molecular weight range of the hydrophobic block and the hydrophilic block is from 800 Da:1 kDa to 3 kDa:5 kDa, 1 kDa:2 kDa to 4 kDa:5 kDa, 1.5 kDa:2 kDa to 4.5 kDa:5 kDa. In some embodiments, the diblock copolymer has at least one hydrophobic block selected from the group consisting of polycaprolactone (PCL), polyvalerolactone (PVL), poly(lactide-co-glycolide) (PLGA), polylactic acid (PLA), polybutyrolactone (PBL), polyglycolide, or polypropiolactone (PPL), and one hydrophilic polymer selected from the group consisting of polyethylene glycol (PEG), hyaluronic acid (HA), or poly-γ-glutamic acid (PGA). Exemplary combinations of diblock copolymers may include, but are not limited to PCL-PEG, PLGA-HA, PVL-PGA, PBL-PEG, and PPL-HA. In some embodiments, the nanoparticle membrane may include one or more diblock copolymers. Employing the diblock copolymer may improve solubility of the breast cancer therapeutic agent in the interior space of the nanoparticle.

In some embodiments of the membrane, the polyvinyl alcohol (PVA) polymer is an emulsifying agent. The polyvinyl alcohol polymer may be employed to promote a fluid membrane of the nanoparticle. The amount of polyvinyl alcohol directly relates to a viscosity of the membrane. The viscosity of the membrane may contribute to a release rate of the breast cancer therapeutic agent from the nanoparticle and may be changed based on a desired release rate of the breast cancer therapeutic agent. The membrane viscosity of the presently described nanoparticle may be 3 mPa·s to 6 mPa·s or 4 mPa·s to 5 mPa·s at 25° C. and 1 atm. The viscosity may be measured by EPR or fluorescence spectroscopy. The polyvinyl alcohol employed in the nanoparticle may have a weight average molecular weight from 85 kDa to 100 kDa or 90 kDa to 95 kDa, and from 0.25 to 5 weight percent, 1 to 4 weight percent, or 2 to 3 weight percent of polyvinyl alcohol (PVA), relative to the total weight of the nanoparticle. The concentration of the PVA may affect the particle size and/or the drug release profile. When the concentration of the PVA is in a range of 0.25 to 0.75 wt %, the average particle size may range from 100-115 nm and the polydispersity of the particles may range from 0.23-0.25. When the concentration of the PVA is in a range of 0.76 to 1.9 wt %, the average particle size may range from 116-140 nm and the polydispersity of the particles may range from 0.20-0.225. When the concentration of the PVA is in a range of 1.91 to 2.9 wt %, the average particle size may range from 141-180 nm and the polydispersity of the particles may range from 0.15-0.199. When the concentration of the PVA is in a range of 2.91 to 5 wt %, the average particle size may range from 181-200 nm and the polydispersity of the particles may range from 0.12-0.149.

Figure 1B:
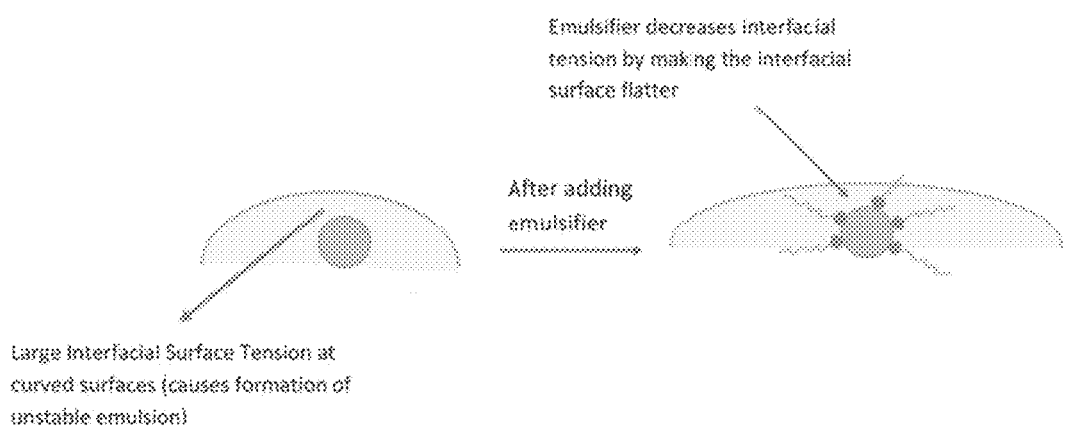
FIG. 1B is a schematic of a method of employing an emulsifier in the method of filling the nanoparticles with the breast cancer therapeutic.

In some embodiments of the nanoparticle, the breast cancer therapeutic agent may include, but is not limited to letrozole, cetuximab, gleevac, idarubicin, trastuzumab, lapatinib, paclitaxel, and/or a salt thereof. In one embodiment, the breast cancer therapeutic agent is not methotrexate. In another embodiment, the breast cancer therapeutic agent is not paclitaxel. In another embodiment, the breast cancer therapeutic agent is not doxorubicin. The nanoparticle may include a mixture of breast cancer therapeutic agents. The breast cancer therapeutic agents may be incorporated into the nanoparticle by emulsification by ultrasonication of the triblock copolymers in solution. FIG. 1A depicts a schematic of a method of filling the nanoparticles with the breast cancer therapeutic. In FIG. 1A and FIG. 1B the PVA may be employed as an added emulsifying agent or emulsifier. The PVA may interact with the drug to allow for a reduced interfacial tension between the drug and the triblock polymer in solution. The PVA may allow for the drug to more easily be encapsulated by the triblock polymer. In some embodiments, the PVA plays a dual role as an emulsifier and as a stabilizing agent. In one embodiment, the presently disclosed nanoparticle is formed by a double emulsion method which includes a drug and water miscible solvent mixture in a mostly oily solution, followed by adding an emulsifier, such as PVA, to the solution. Then the drug and water miscible solvent are diluted into a mostly aqueous solution, the action may encapsulate the drug inside a mostly oily membrane assisted by the emulsifier and the drug inside the membrane can be removed from the aqueous solution. This method of preparation provides for a slow release rate of a drug from the membrane due to the PVA stabilizing the membrane and solvent interaction. For example, to accomplish a double emulsion there is a first and second emulsion. A first mixture of the triblock polymers, the drug, and a 0.5% to 5%, 0.75% to 4%, or 1% to 2% final concentration of PVA may be combined in a solution (first emulsion). The first mixture may then be diluted by 10 times to 30 times with a 5% to 40%, 10% to 30%, or 15% to 20% lower concentration of PVA in an aqueous solution (second emulsion), then mixed and evaporated to form the final nanoparticles. The mixing may be by ultrasonication, sonication, or mechanical mixing and obtaining the final solid nanoparticles by, for example, centrifugation and removal of solvents, by siphoning, evaporation or both.

Figure 2:
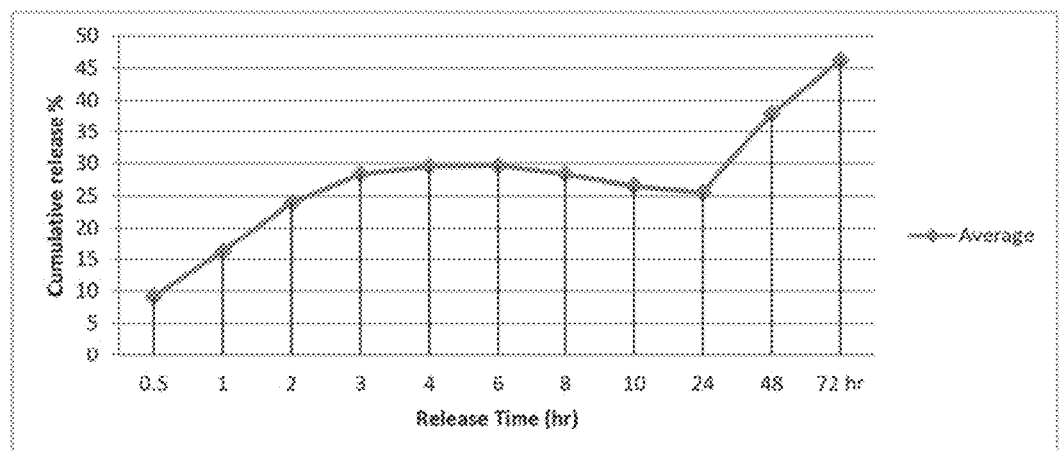
FIG. 2 is a graph of an exemplary release rate of a breast cancer therapeutic from the nanoparticle.

By the method of emulsification by ultrasonication, the breast cancer therapeutic agent is incorporated into the nanoparticle at 0.5 to 10 weight percent, 1 to 8 weight percent, 3 to 7 weight percent, or 4 to 6 weight percent, relative to the nanoparticle. The quantity of the breast cancer therapeutic that is required for the treatment may be dictated by the efficiency by which the nanoparticle is retained in a breast cancer patient's blood and the drug release rate of the nanoparticle. In some embodiments, the nanoparticle has an internal volume of 1 picoliter to 1 nanoliter, 10 picoliter to 750 picoliter, 100 picoliter to 500 picoliter, or 250 picoliter to 400 picoliter. In some embodiments, a rate of release of the breast cancer therapeutic agent is a cumulative percent of volume, relative to the total incorporated breast cancer therapeutic agent in the nanoparticle, 25% to 75%, 35% to 65%, or 45% to 55% in 24 hours to 96 hours, 36 hours to 72 hours, 48 hours to 60 hours. FIG. 2 depicts a graph of an exemplary release rate of a breast cancer therapeutic agent from the nanoparticle. In some embodiments within 24 hours 10%-40% of the drug volume may be released in a patient. The breast cancer therapeutic agent may be released through the pores of the membrane. The pores of the membrane may have a diameter in a range of 0.1-10 nm, 0.5-10 nm, 1-9 nm, 2-8 nm, or 3-6 nm.

The presently disclosed nanoparticle may be stable for storage for 100 to 130 days. The nanoparticles may be stored in water (e.g., distilled water, deionized water, doubly distilled water) and kept at a temperature in a range of 0-10° C., 0-5° C., or 3-5° C. The presently disclosed nanoparticle, which is optionally loaded with the breast cancer therapeutic agent, may have a polydispersity of, for example, 0.1 to 0.2, 0.12 to 0.18, or 0.14 to 0.16.

The polymersome as described herein has a hydrophobic exterior surface. The hydrophobic exterior surface may not be easily solubilized in an in vivo application by injection into the blood stream of a cancer patient. To increase solubility of the nanoparticle, a bovine serum albumin (BSA) is included in the presently disclosed nanoparticle. BSA is a protein derived from cows, having 583 amino acid residues in length and a molecular weight of 66.5 kDa. In some embodiments, the BSA is, relative to the total weight of the nanoparticle, 0.5 to 8 weight percent, 1 to 7 weight percent, 2 to 6 weight percent, or 3 to 5 weight percent. The BSA may contact the exterior membrane of the polymersome or the outside of the nanoparticle. The contact may be by non-specific interactions or van der Waals interactions between non-polar amino acids on the surface of the BSA protein and the hydrophobic PLA copolymer block. Embodiments of the nanoparticle prior to incorporating the breast cancer therapeutic agent into the interior space (FIG. 3), may have a diameter of 100 nm to 170 nm, 110 nm to 160 nm, 125 nm to 150 nm, or 135 nm to 140 nm. Embodiments of the nanoparticle after incorporating the breast cancer therapeutic agent into the interior space (FIG. 4) may have a diameter of 190 nm to 210 nm, or 200 nm to 205 nm. Embodiments of the nanoparticle having the BSA on the exterior surface (FIG. 5), may have a diameter of 290 nm to 312 nm, 295 nm to 310 nm, or 300 nm to 305 nm. Embodiments of the nanoparticle having the BSA on the exterior surface and the breast cancer therapeutic agent in the interior space may have a diameter of 130 nm to 170 nm, or 140 nm to 160 nm (FIG. 6). The polydispersity of such nanoparticles may be in a range of 0.2-0.6, 0.2-0.5, 0.2-0.4, or 0.25-0.35.

Aggregation may result in an ineffective nanoparticle for drug delivery. Zeta potential is the measurement of an electrical potential of the exterior surface of a nanoparticle. A higher (more negative) electrical potential of the exterior surface may prevent nanoparticle aggregation by creating an electronic barrier (electrostatic repulsion) between nanoparticles. An absolute value of electrical potential or zeta potential directly correlates to the non-aggregating potential of the nanoparticle. The presently disclosed nanoparticle has a zeta potential of −7 mV to −20 mV, −10 mV to −18 mV, or −12 mV to −15 mV. FIG. 7 and FIG. 8 depict tables of the zeta potentials of nanoparticles prior to incorporating the breast cancer therapeutic agent into the interior space and the zeta potential of the nanoparticles after the breast cancer therapeutic agent is incorporated into the interior space, respectively.

The presently disclosed nanoparticle may further include a cancer targeting agent. A cancer targeting agent may be biologically active macromolecules (e.g., monoclonal antibodies such as bevacizumab, cetuximab, or ipilimumab) or small molecules (e.g. folate). Small molecules may be recognized by surface protein receptors that are uniquely expressed or overexpressed on cancer tumors or in tumor related tissues or may be targeted to proteins and receptors inside the cancer cell, such as seliciclib, imatinib, or bortezomib. Macromolecules may recognize surface proteins and peptides that are uniquely expressed or overexpressed on cancer tumors or in tumor related tissues.

In some embodiments, the cancer targeting agent is an anti-Her2 antibody contacting the outer surface or exterior surface of the nanoparticle. Her2 is a growth factor receptor and biomarker for certain aggressive breast cancers. Her2 may be overexpressed in 15% to 30% of breast cancers. As used herein "antibody" or "antibodies" may include a full antibody including the heavy and light chains or only portions of the full antibody such as only a heavy chain, only a light chain, or only the functional antigen-binding (Fab) domains. The anti-Her2 antibody may be monoclonal or polyclonal. The anti-Her2 antibody may be sourced from a mouse, a rabbit, a chicken, or combinations thereof.

In one embodiment, the antibody may be covalently attached to the nanoparticle membrane by a biotin-avidin complex. Biotin may be attached to the triblock copolymers via an ester bond with biotin, and avidin may label the antibody. The avidin-biotin complex is the strongest known non-covalent interaction ($K_d=10^{-15}$ M) between a protein and ligand. The bond formation between biotin and avidin is very rapid, and once formed, is unaffected by extremes of pH, temperature, organic solvents and other denaturing agents. Avidin may further be monovalent (i.e. binding site for one biotin molecule) or divalent (i.e. two binding sites for one biotin molecule each) for the present application, however avidin may have up to tetravalency. Relevant to the present disclosure, for example, a divalent avidin may be attached to an anti-Her2 antibody via a biotin on the anti-Her2 antibody, purified, and then mixed with the polymersome having a biotin conjugated to a triblock copolymer by chemical methods familiar to those in the art. Other mechanisms of attaching antibodies to the copolymers include thiolation of antibodies with 3-(2-pyridyldithio)propionic acid-N-hydroxysuccinimide ester (SPDP), followed by deprotection with dithiothreitol (DTT) and conjugation to the triblock copolymers covalently bonded to maleimide. Additional methods familiar in the art may be used as well. See Antibody Conjugation Methods for Active Targeting of Liposomes, Chapter 4 of "Methods in Molecular medicine. Vol. 25: Drug Targeting: Strategies, Principles, and Applications," Edited by G. E. Francis and C. Delgado © Humana Press Inc. Totawa, N.J., incorporated by reference herein in its entirety. Antibody attached to triblock copolymers may be a percentage by weight relative to the total nanoparticle of 25%-75%, 30%-60%, or 40%-50%.

In some embodiments, the anti-Her2 antibody may contact a surface of the nanoparticle by non-specific molecular interactions or van der Waals interactions. The coupling by non-specific interaction may be accomplished by combining a 15% to 25% or 18% to 20% by volume of anti-Her2 antibody in solution with nanoparticles of $5.5 \times 10^{-4}$ to $7 \times 10^{-4}$ particles/mL, or $6 \times 10^{-4}$ to $6.5 \times 10^{-4}$ particles/mL and mixed in a shaker for 10-120 mins, 30-90 mins, or 50-70 mins at 20-50° C., 30-50° C., or 35-45° C. The volume of anti-Her2 antibody in solution may be in a range of 10-200 µL, 10-100 µL, or 40-60 µL. The volume of the nanoparticles solution may be in a range of 100-300 µL, 150-250 µL, or 175-225 µL. The nanoparticles/anti-Her2 mixture may be dialyzed for one hour to six hours or two hours to four hours to remove the excess anti-Her2 antibody by employing a single sided dialysis chamber and a nitrocellulose membrane cut off of from 250 kDa-300 kDa. The dialysis buffer may be a pH of 6.25 to 7.25, and a phosphate based buffer, such as PBS. The buffer may be exchanged three times every 1.5 hours to two hours.

Another aspect of the disclosure relates to a method of down regulating expression of a gene in a breast cancer cell line (e.g., MCF-7, 600MPE, AU565, BT-20, BT-474, BT-483, BT-549, Evsa-T, Hs578T, MDA-MB-231, SkBr3, and T-47D). The breast cancer cells may be incubated with the drug-loaded nanoparticles for 4-100 hours, 10-90 hours, 20-80 hours, or 30-75 hours. The concentration of the drug-loaded nanoparticles may range from 0.0001-10 µM, 0.0005-1 µM, 0.001-0.5 µM, or 0.002-0.1 µM.

Exemplary genes include antiapoptotic genes such as Bcl-2, Bcl-XL, Mcl-1, CED-9, A1, Bfl-1, MAPK3, and c-MYC. Pre-designed primers for the genes of interest may be commercially available. Real-time PCR for the antiapoptotic genes may be performed to ensure the delivery of the drug by the nanoparticles. The gene expression levels may be quantitated using the delta-delta CT ($\Delta\Delta^{CT}$) method and optionally further re-calculated manually. The gene expression level may be normalized to a housekeeping gene: glyceraldehydes-3-phosphate dehydrogenase (GAPDH). The gene expression level may range from −1 to +0.1, −0.8 to −0.1, −0.7 to −0.2, or −0.5 to −0.3.

Figures 3A, 3B:
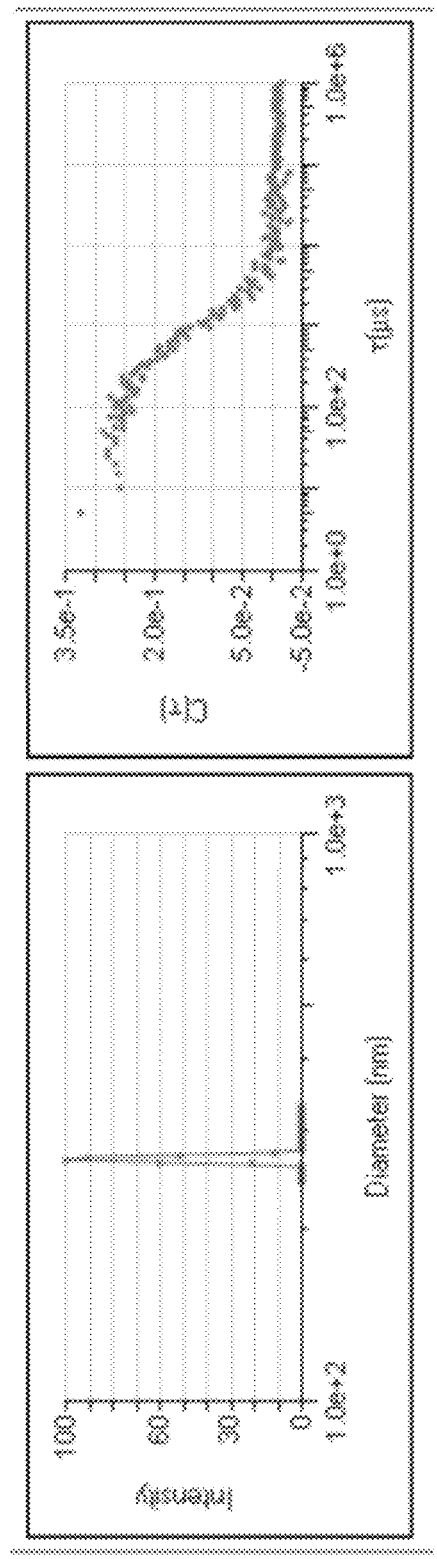
FIG. 3A is a diagram of exemplary data on the diameter of nanoparticles having a breast cancer therapeutic agent incorporated in to the nanoparticles and having an anti-Her2 antibody contacting the exterior surface of the nanoparticle.
FIG. 3B is a scatter plot of the counts of nanoparticles that are eluted from a dynamic light scattering chromatography column.

The nanoparticle including the antibody contacting the exterior surface may have a diameter of 300 nm to 370 nm, 310 nm to 350 nm, or 325 nm to 340 nm (FIG. 3A and FIG. 3B). The polydispersity of such nanoparticles may be in a range of 0.2-0.6, 0.3-0.6, 0.3-0.5, or 0.4-0.5.

FIG. 4A and FIG. 4B depict scanning electron micrographs of an embodiment of crystallized nanoparticles prior to incorporating the breast cancer therapeutic agent into the interior space at 1,200× magnification and 24,000× magnification. FIG. 5A and FIG. 5B depict scanning electron micrographs of crystallized nanoparticles prior to incorporating the breast cancer therapeutic agent into the interior space at 15,000× magnification and 100,000× magnification. FIG. 6 depicts scanning electron micrographs of an embodiment of crystallized nanoparticles after incorporating the breast cancer therapeutic agent into the interior space at 65,000× magnification.

Figure 7A:
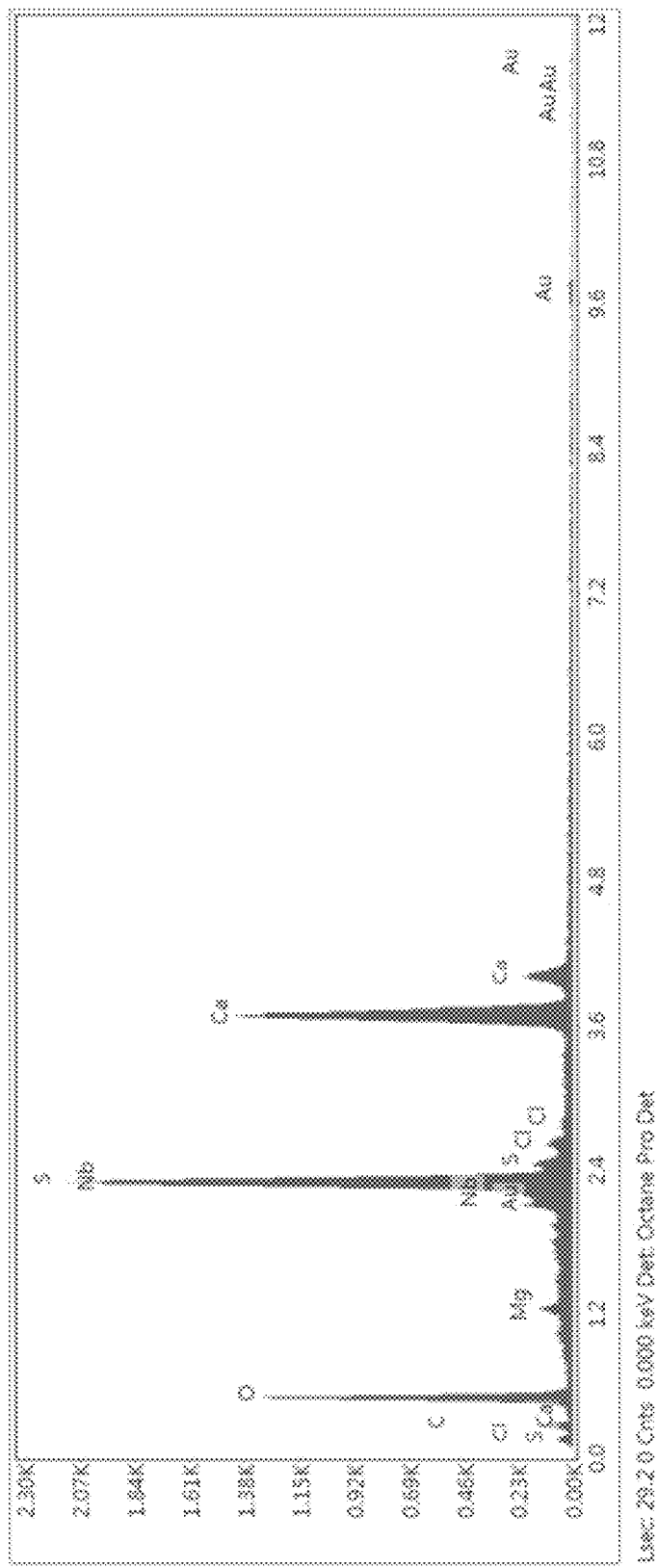
FIG. 7A is an X-ray photoelectron spectroscopy (XPS) scan of the crystallized surface of the nanoparticle pictures in FIG. 7B.
Figure 7B:
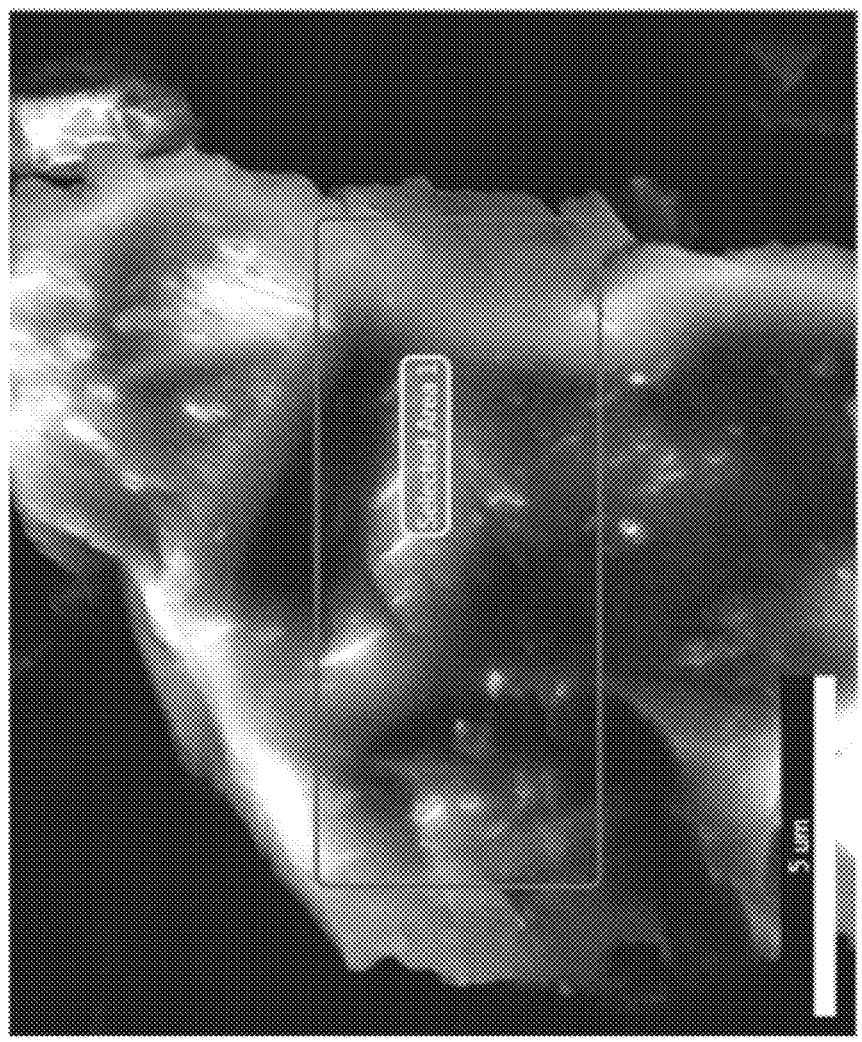
FIG. 7B is scanning electron micrograph of an embodiment of crystallized nanoparticles.
Figure 8A:
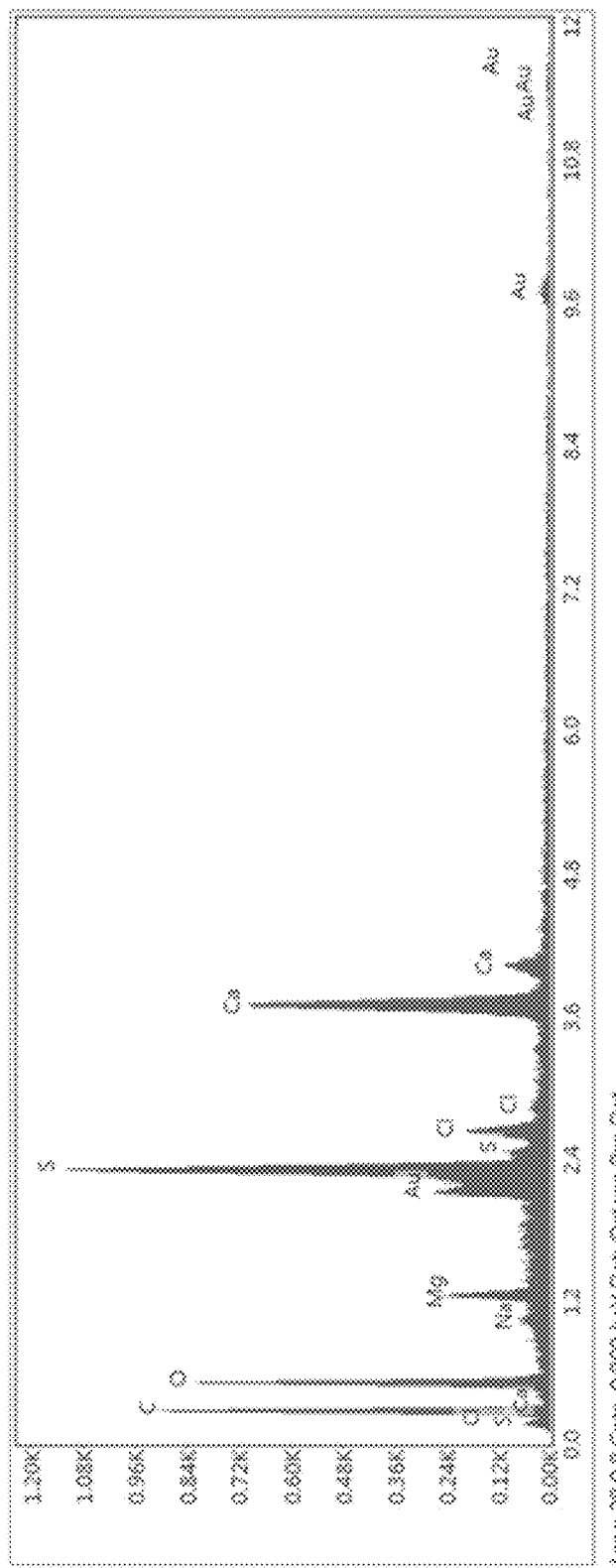
FIG. 8A is an XPS scan of the crystallized surface of the nanoparticle pictures in FIG. 8B.
Figure 8B:
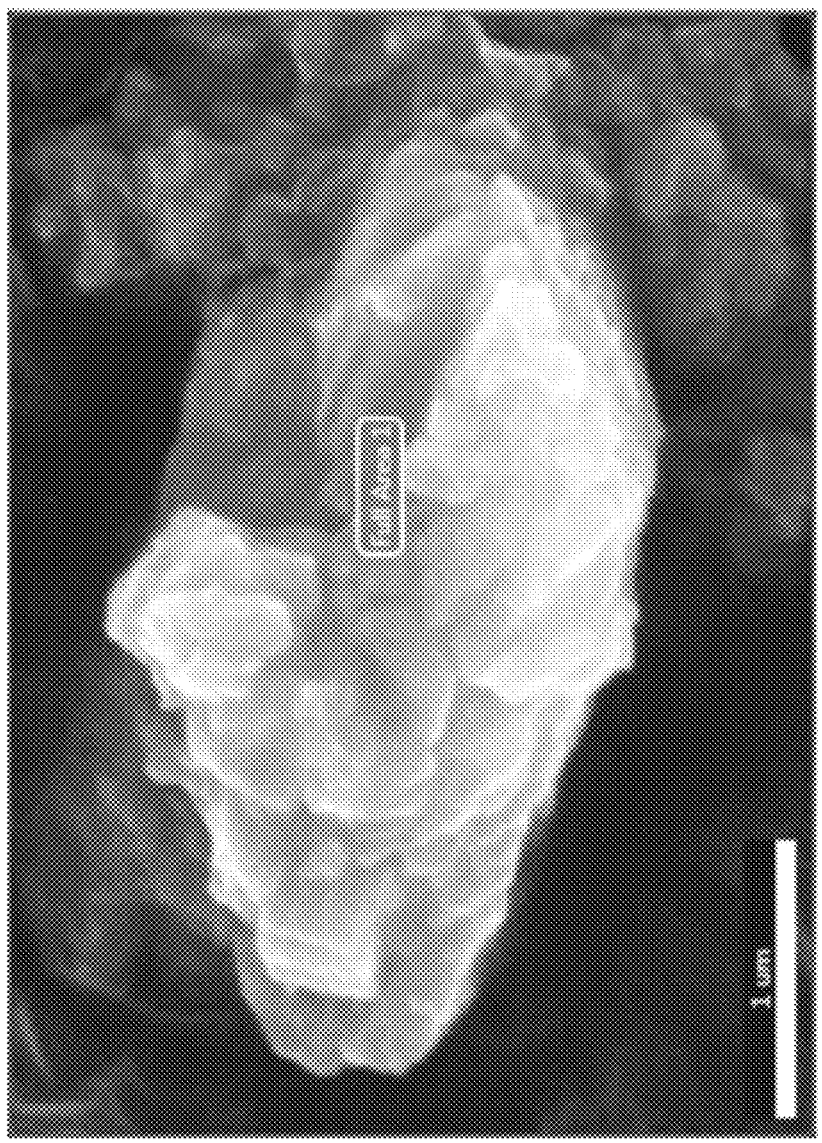
FIG. 8B is scanning electron micrograph of an embodiment of crystallized nanoparticles.

FIG. 7A and FIG. 8A are X-ray photoelectron spectroscopy (XPS), or a surface-sensitive quantitative spectroscopic technique, that measures the elemental composition of the crystallized surface of the nanoparticle pictures in FIG. 7B and FIG. 8B, respectively.

FIG. 9A, FIG. 9B, and FIG. 9C depict scanning electron micrographs of an embodiment of crystallized complete nanoparticles at 50,000× magnification, 5,000× magnification, and 70,000× magnification, respectively. FIG. 10 depicts a scanning electron micrograph of an embodiment of crystallized nanoparticles after incorporating the breast cancer therapeutic agent into the interior space at a 700× magnification.

Figure 11A:
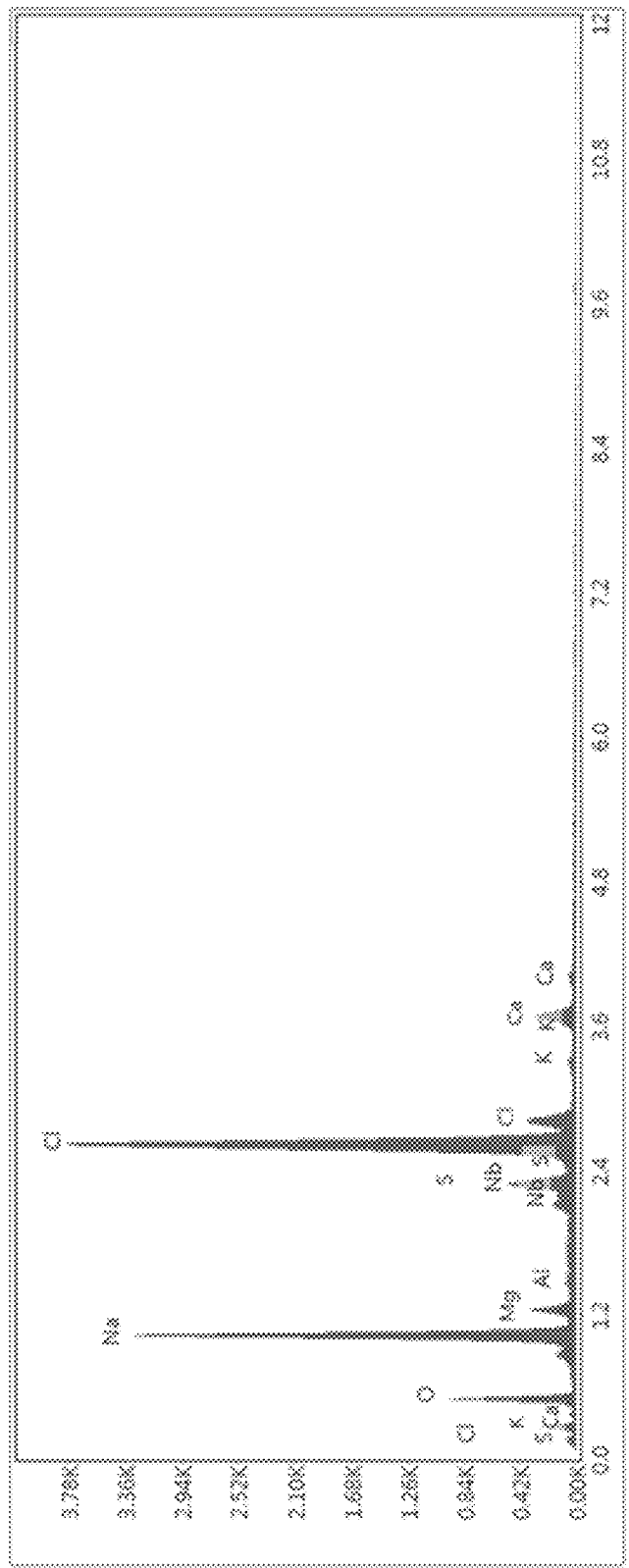
FIG. 11A is a XPS of the crystallized surface of the nanoparticle pictures in FIG. 11B.
Figure 11B:
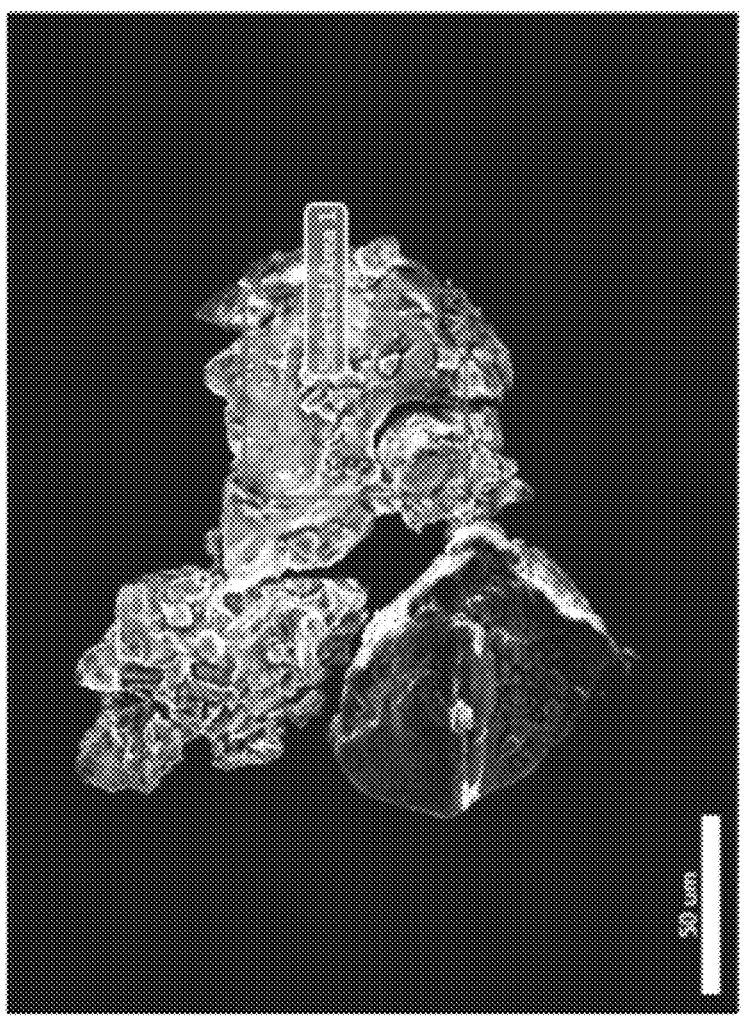
FIG. 11B is a scanning electron micrograph of an embodiment of crystallized nanoparticles.
Figure 12A:
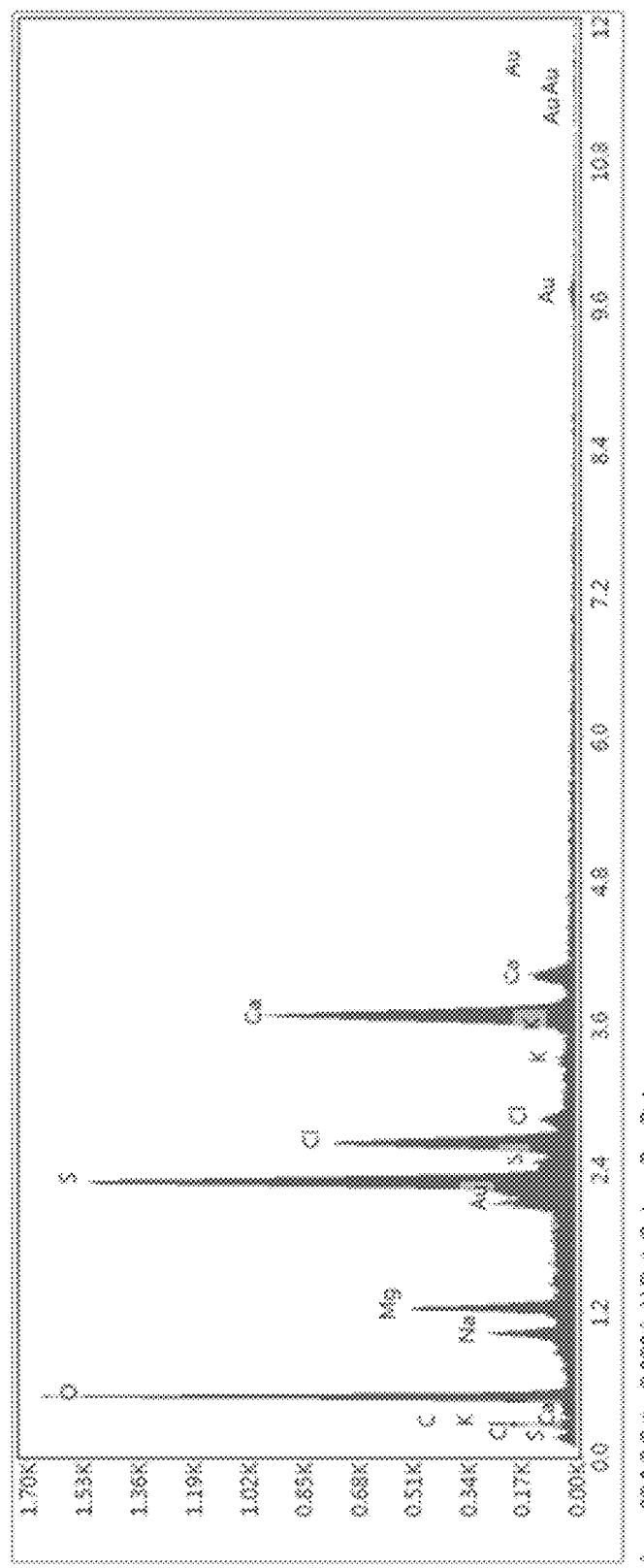
FIG. 12A is a XPS of the crystallized surface of the nanoparticle pictured in FIG. 12B.
Figure 12B:
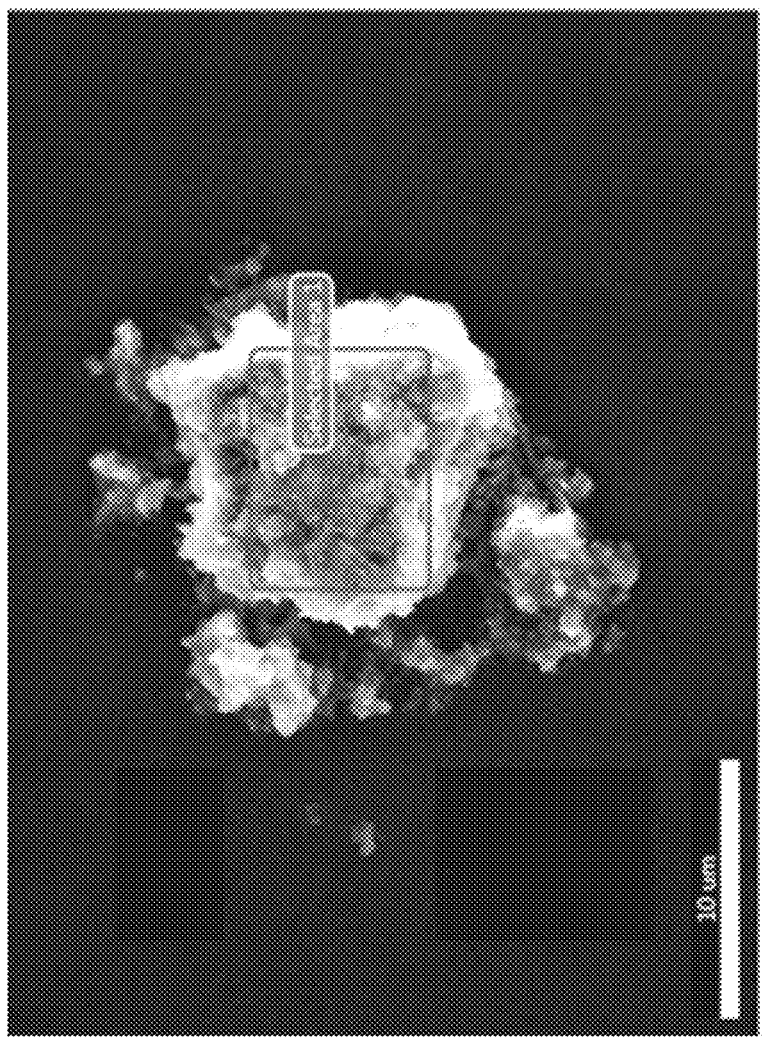
FIG. 12B is a scanning electron micrograph of an embodiment of crystallized nanoparticles.

FIG. 11A and FIG. 12A are X-ray photoelectron spectroscopy (XPS), or a surface-sensitive quantitative spectroscopic technique, that measures the elemental composition of the crystallized surface of the nanoparticle pictures in FIG. 11B and FIG. 12B, respectively.

Figure 13:
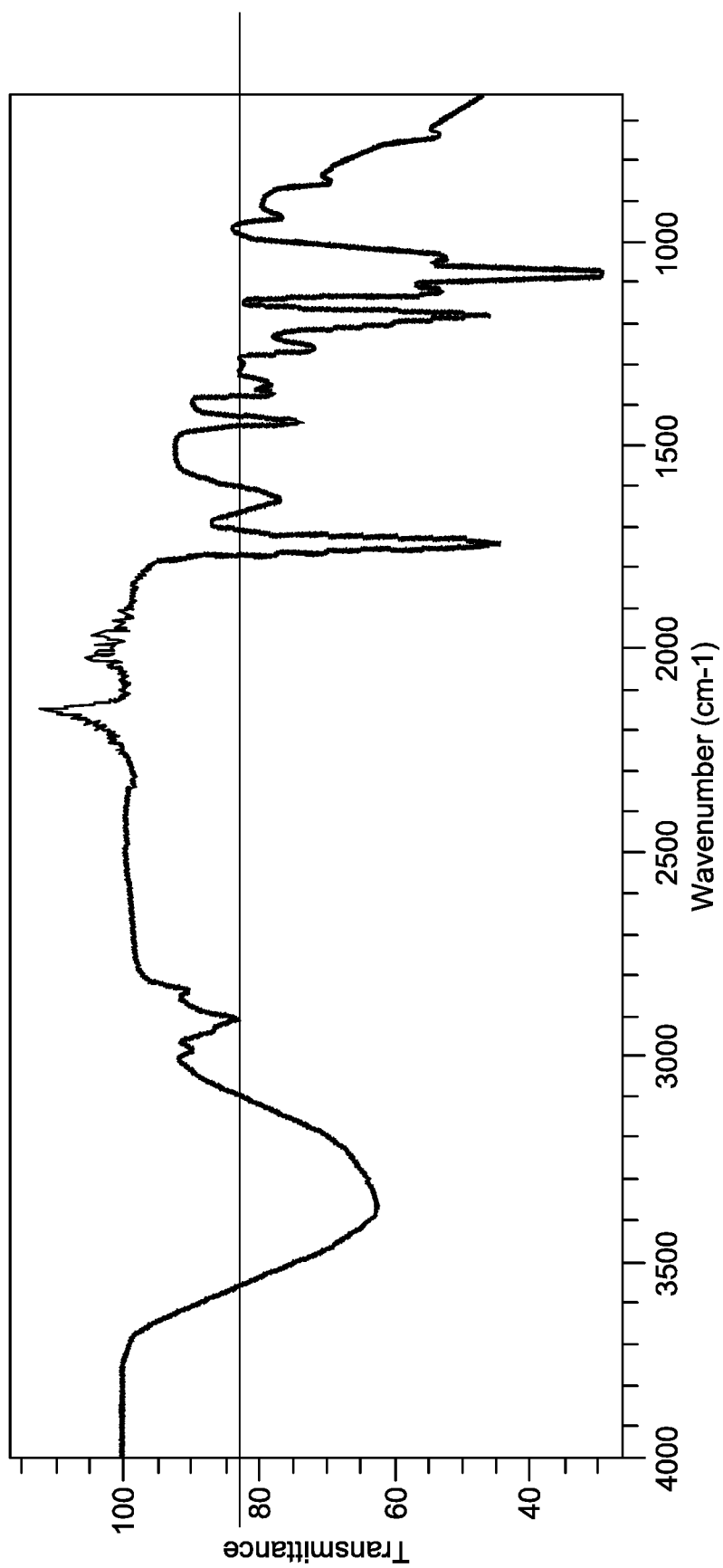
FIG. 13 is a Fourier Transform Infrared spectrum of an embodiment of nanoparticles prior to incorporating the breast cancer therapeutic agent into the interior space.
Figure 14:
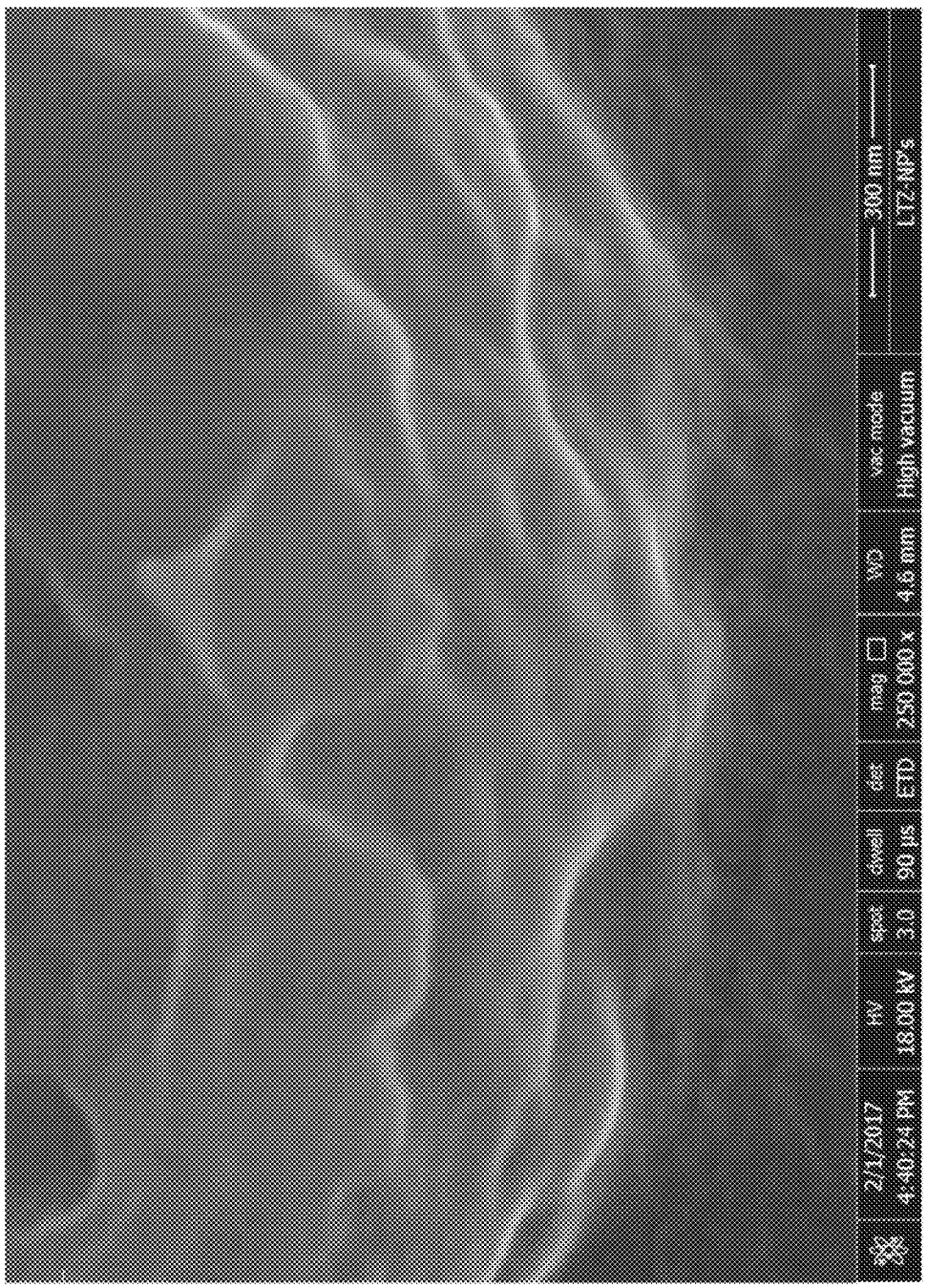
FIG. 14 is a scanning electron micrograph of an embodiment of crystallized nanoparticles after incorporating the breast cancer therapeutic agent into the interior space at 250,000× magnification.
Figure 15:
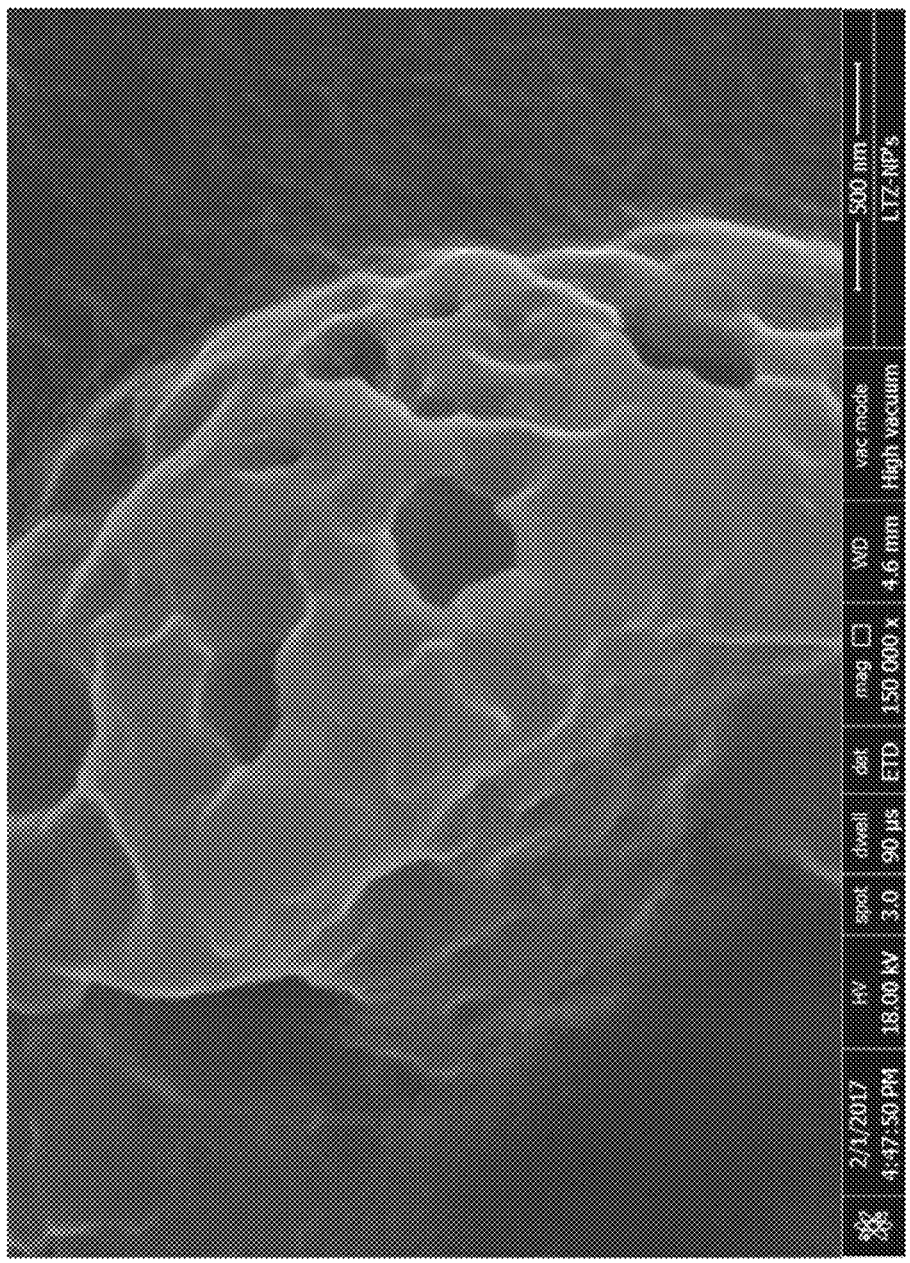
FIG. 15 is a scanning electron micrograph of an embodiment of crystallized nanoparticles after incorporating the breast cancer therapeutic agent into the interior space at 150,000× magnification.
Figure 16:
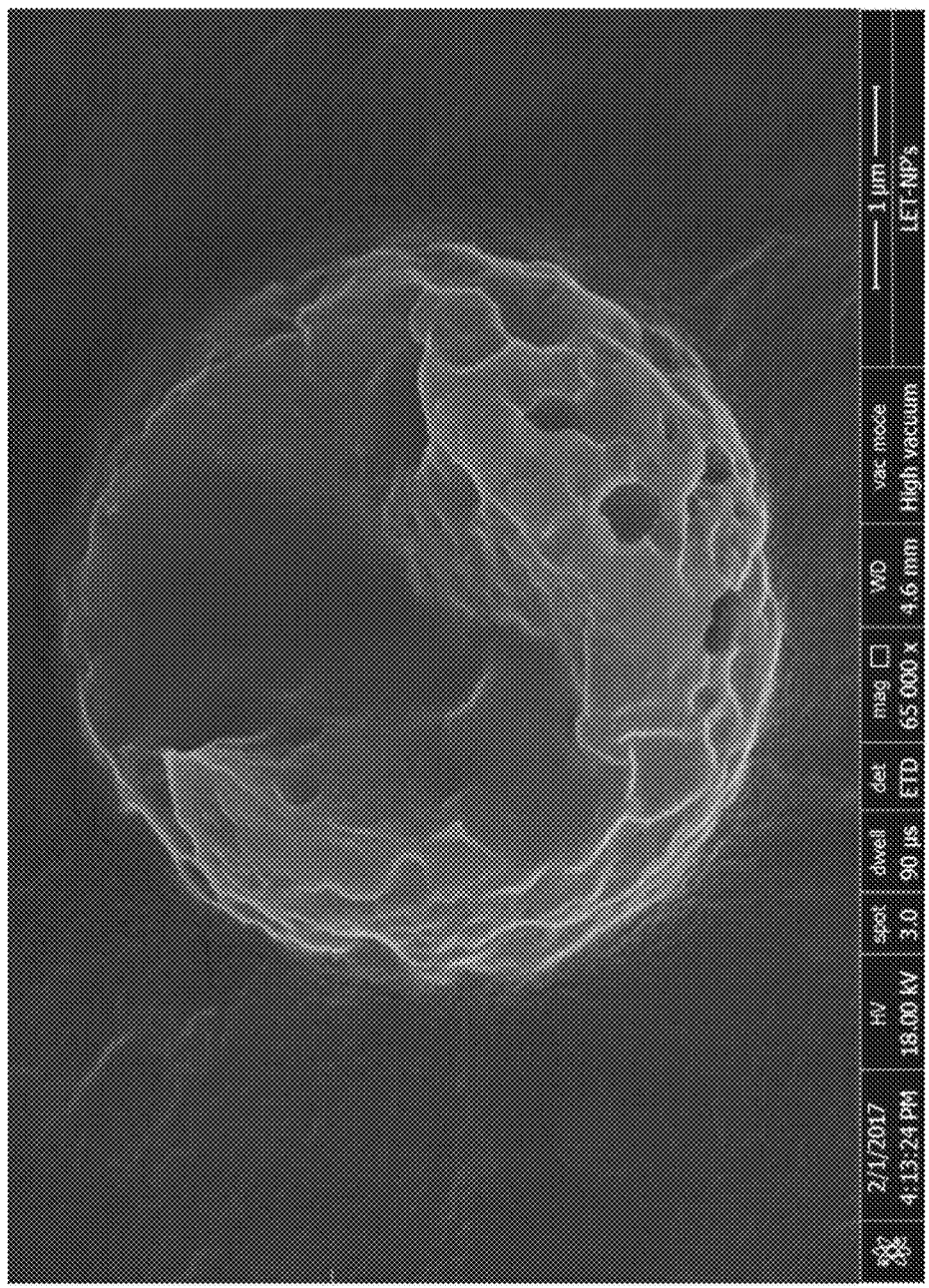
FIG. 16 is a scanning electron micrograph of an embodiment of crystallized nanoparticles after incorporating the breast cancer therapeutic agent into the interior space at 65,000× magnification.
Figure 17:
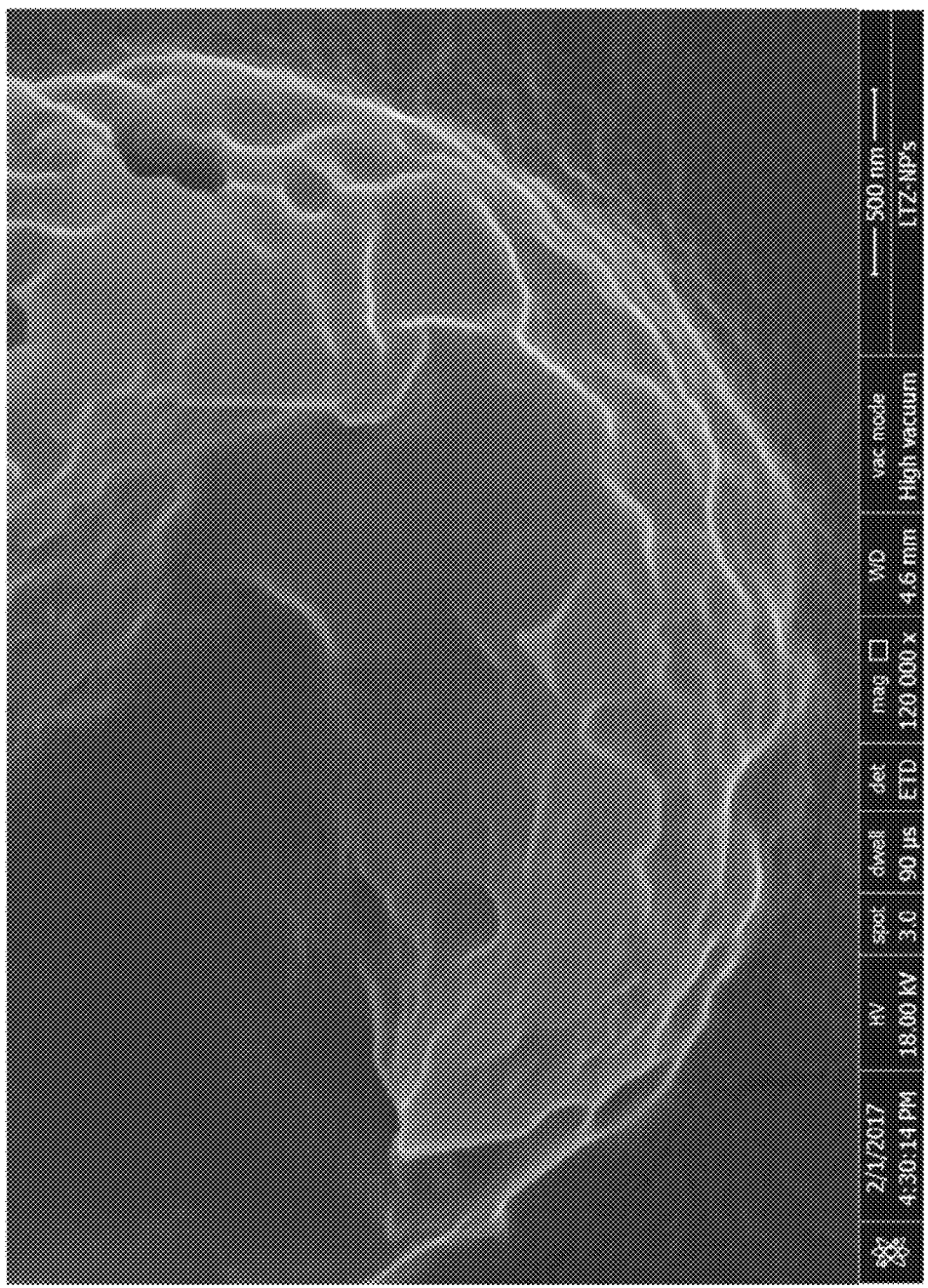
FIG. 17 is a scanning electron micrograph of an embodiment of crystallized nanoparticles after incorporating the breast cancer therapeutic agent into the interior space at 120,000× magnification.

FIG. 13 is a Fourier Transform Infrared spectrum of an embodiment of nanoparticles prior to incorporating the breast cancer therapeutic agent into the interior space.

Figure 18:
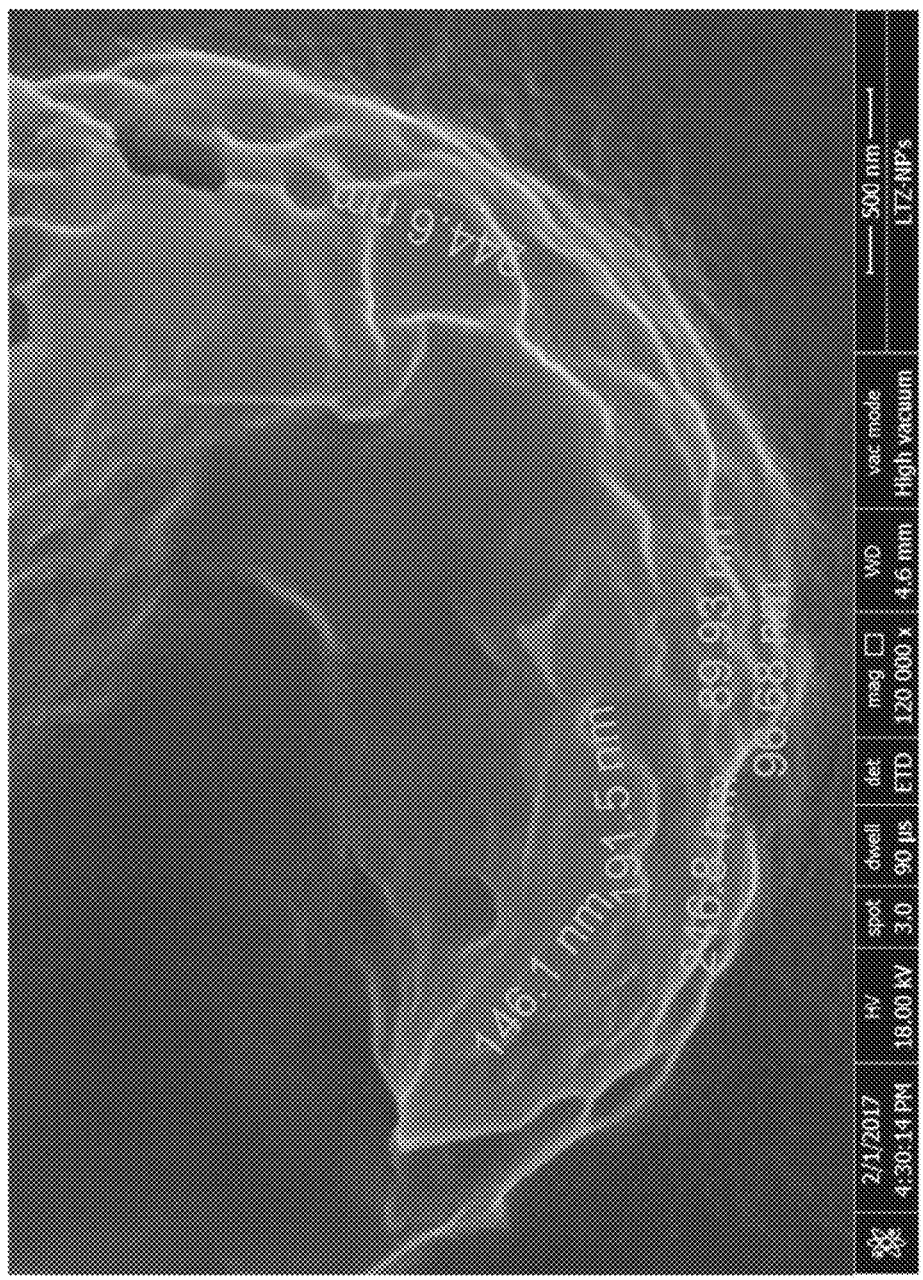
FIG. 18 is a scanning electron micrograph of an embodiment of crystallized nanoparticles after incorporating the breast cancer therapeutic agent into the interior space at 120,000× magnification.

FIGS. 14, 15, 16, 17, and 18 are scanning electron micrographs of an embodiment of crystallized nanoparticles after incorporating the breast cancer therapeutic agent into the interior space at 250,000× magnification, 150,000× magnification, 65,000× magnification, 120,000× magnification, and 120,000× magnification, respectively. The measurements displayed in FIG. 18 represent the diameter (in nanometers) of the crystallized nanoparticles located on a main crystal.

Figure 19:
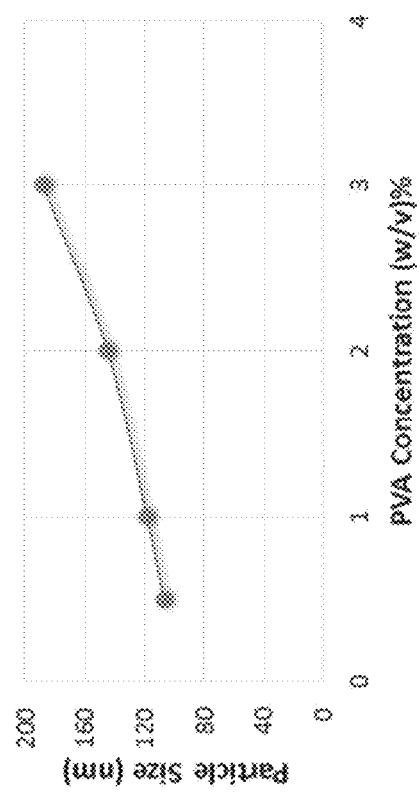
FIG. 19 is a graph showing the correlation between the concentration of PVA and the particle size.

FIG. 19 shows the variation of PVA concentrations and its effect on particle size.

Figure 20:
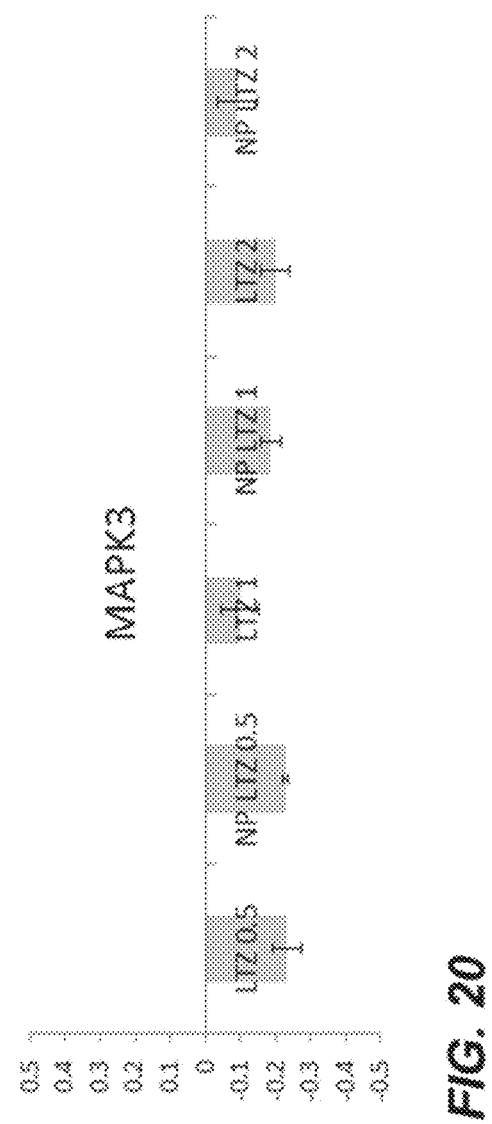
FIG. 20 is a graph showing the expression of MAPK3 gene in the presence of encapsulated Letrozole and free Letrozole.
Figure 21:
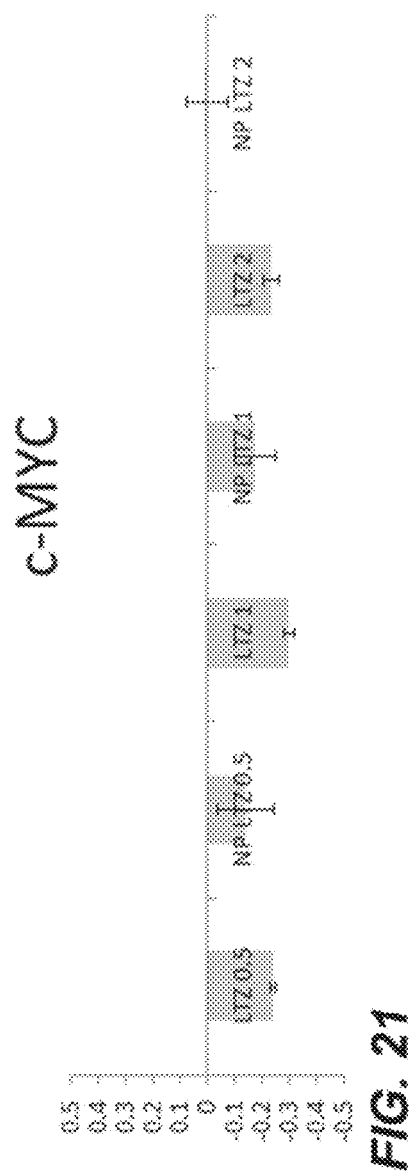
FIG. 21 is a graph showing the expression of c-MYC gene in the presence of encapsulated Letrozole and free Letrozole.

FIGS. 20 and 21 show the gene expression results. In FIG. 20, each bar represents the expression of MAPK3 gene in the presence of each sample. In FIG. 21, each bar represents the expression of c-MYC gene in the presence of each sample.

The presently disclosed nanoparticle may be administered to a patient from once weekly to four times weekly or two times weekly to 3 times weekly at a therapeutically effective amount. Preferably, the nanoparticle is administered twice weekly (e.g., every 3 days). The nanoparticles may be administered intravenously or intra-arterially. In some implementations, a pharmaceutical composition of the presently disclosed nanoparticle may include injectable preparations. For example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use. In some embodiments, the nanoparticles may be applied directly to the surface of a tumor or an area of tissue surrounding an excised tumor of a patient on a surgical bed by a surgeon. The nanoparticles may be sprayed in a solution or dispersed by a brush, dropper, or paste onto the surface of a tumor or to the area of tissue surrounding an excised tumor during a surgical procedure in a living patient. The surgeon may inject the nanoparticles in a sterile solution, as described herein, into a blood vessel entering a tumor.

In certain embodiments of the presently disclosed nanoparticle, a "therapeutically effective amount" of the nanoparticle is that amount effective for treating, alleviating, ameliorating, relieving, delaying onset of, inhibiting progression of, reducing severity of, and/or reducing incidence of one or more symptoms or features of breast cancer.

In some implementations of therapeutic protocols involve administering a therapeutically effective amount of the presently disclosed nanoparticle to a healthy individual (i.e., a subject who does not display any symptoms of cancer and/or who has not been diagnosed with cancer). For example, healthy individuals may be injected with the nanoparticle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, the nanoparticles described herein can be used to inhibit the growth of cancer cells, e.g., breast cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

The presently disclosed nanoparticle, may first interact with a cancer tumor expressing the Her2 receptor. For example, the presently disclosed nanoparticle while circulating in the blood stream may interact specifically with a tumor or cell proximal to a tumor expressing the Her2 receptor. In some implementations, such as a surgeon dispersing the nanoparticles directly on to a tumor in a surgical bed of a patient, the nanoparticles coupled to the anti-Her2 antibody may recognize a Her2 receptor on a cell on the surface of the tumor. The antibody against Her2 on the surface of the antibody may interact with the Her2 receptor on the cell and become internalized into an endosome or lysosome upon binding the cell. Once internalized the nanoparticle may begin to release the drug into the cell lysosome or endosomes. In some embodiments, the nanoparticle may not release the drug until the nanoparticle is in the intracellular space and cannot release the drug in an endosome or lysosome. The nanoparticle may persist in the cell and slowly release the drug over duration as described herein.

The examples below are intended to further illustrate the preparation of the nanoparticles and are not intended to limit the scope of the claims.

Example 1

Materials
Polylactide-block-poly(ethylene glycol)-block-poly lactide triblock (PLA average Mn=1,500, PEG average Mn=900), Letrozole (Mw=285.30 g), chloroform, poly(vinylalcohol) (Mw=89,000-98,000; 99% hydrolyzed), bovine serum albumin (lyophilized powder ≥96%), and Anti-Her2 produced in rabbit were obtained from Sigma-Aldrich and were used as received.
Equipment
Probe sonicator (UltraSonic Processor, Sonic VCX 130)
Centrifuge (Thermo Scientific Centrifuge)
Particle size analyzer (Brookhaven instruments)
Zetasizer
UV Spectrophotometer (Thermo-Evolution UV 60S, Thermo Scientific)
Rotary Evaporator (Buchi)
Synthesis of PEG-PLA nanoparticles, Polylactide-block-poly(ethylene glycol)-block-polylactide Void PEG-PLA nanoparticles were synthesized using 10 mg PEG-PLA: 10.5 mg was dissolved in 1 ml chloroform. 200 ul of DMSO was added and ultrasonication was performed (100%, 30 s). 2 ml of 3% PVA was then added and ultrasonication was performed (100%, 30 s). The solution was then diluted with 20 ml of 0.3% PVA. The 22 ml was then divided into 11×2 ml to be centrifuged in the mini spin. Tubes were then centrifuged at 11,000 rpm for 1 hour. Pellet was then washed 3 times as following: supernatant was decanted, 1 ml of distilled water was added, ultrasonication was performed (70%, 5 s), and then centrifuged for 1 hour at 11,000 rpm. After the final washing step, supernatant was discarded and pellet were left to dry. Water was then added to the pellets to be dissolved, and nanoparticles solution was collected in a 50 ml falcon tube and stored at 4° C. Data of exemplary void nanoparticles are exhibited in Table 2 and Table 3.

TABLE 2

Exemplary empty/void nanoparticle (NP) data

| Type | Sample ID | Eff. Diam. (nm) | Poly-dispersity | Baseline Index |
|---|---|---|---|---|
| DLS | void NPs soln 002 - 5 | 146.02 | 0.18 | 4.04 |
| DLS | void NPs soln 002 - 4 | 152.07 | 0.17 | 2.47 |
| DLS | void NPs soln 002 - 3 | 151.06 | 0.21 | 1.14 |
| DLS | void NPs soln 002 - 2 | 150.37 | 0.16 | 0.92 |
| DLS | void NPs soln 002 - 1 | 150.89 | 0.16 | 1.23 |
| | Mean: | 150.08 | 0.18 | 1.96 |
| | Std Err: | 1.05 | 0.01 | 0.59 |
| | Std Dev: | 2.35 | 0.02 | 1.31 |

TABLE 3

Exemplary empty/void nanoparticle data on zeta potential

| Type | Sample ID | Zeta Potential (mV) | Mobility (μ/s)/(V/cm) | RMS Residual |
|---|---|---|---|---|
| PALS | void NPs soln 002 - 5 | −17.45 | −1.36 | 3.01E−02 |
| PALS | void NPs soln 002 - 4 | −17.31 | −1.35 | 1.48E−02 |
| PALS | void NPs soln 002 - 3 | −19.32 | −1.51 | 2.43E−02 |
| PALS | void NPs soln 002 - 2 | −16.50 | −1.29 | 2.65E−02 |
| PALS | void NPs soln 002 - 1 | −22.65 | −1.77 | 2.07E−02 |
| | Mean: | −18.64 | −1.46 | 2.33E−02 |
| | Std Err: | 1.10 | 0.09 | 2.61E−03 |
| | Std Dev: | 2.47 | 0.19 | 5.84E−03 |

Synthesis of Letrozole-Loaded Nanoparticles

To prepare Letrozole-loaded nanoparticles, a 15.2 mg (±0.1) of the polymer was weighed and dissolved in 1 mL chloroform ($CHCl_3$) solvent. A solution of Letrozole was prepared by dissolving 4.3 mg (±0.1) of Letrozole in 4 mL of DMSO. A 200 μl of Letrozole solution was emulsified in the polymer solution by ultrasonication using 2 mm probe (30 s, 100% power). 2.0 mL of 3% PVA was added to the solution and also was emulsified by ultrasonication using 2 mm probe (30 s, 100% power). The resulted emulsion was then diluted by adding 20 mL of 0.3% PVA. The obtained white emulsion solution was divided over 14 (1.5 mL) Eppendorf tubes and was centrifuged for one hour on 11,000 rpm. The obtained white precipitate was then washed and centrifuged for one hour on 11,000 rpm three times. After the third wash the obtained pellets were left to dry and then collected, weighed and stored at 4° C. fridge. Data of exemplary void nanoparticles are exhibited in Table 4 and Table 5.

TABLE 4

Exemplary Letrozole-loaded nanoparticle data

| Type | Sample ID | Eff. Diam. (nm) | Poly-dispersity | Baseline Index |
|---|---|---|---|---|
| DLS | Letrozole-loaded NPs 002 - 5 | 209.82 | 0.18 | 0.00 |
| DLS | Letrozole-loaded NPs 002 - 4 | 207.39 | 0.15 | 0.70 |
| DLS | Letrozole-loaded NPs 002 - 3 | 197.52 | 0.12 | 0.00 |
| DLS | Letrozole-loaded NPs 002 - 2 | 195.88 | 0.14 | 2.94 |
| DLS | Letrozole-loaded NPs 002 - 1 | 195.95 | 0.14 | 4.28 |
| | Mean: | 201.31 | 0.15 | 1.59 |
| | Std Err: | 3.02 | 0.01 | 0.86 |
| | Std Dev: | 6.75 | 0.02 | 1.93 |

The zeta potential and the electrophoretic mobility were measured using a ZetaPALS potential analyzer (Brookhaven instruments, Holtsville, N.Y., USA). The results are displayed in Table 5. The zeta potentials of LTZ-loaded NPs were all in the negative range, indicating the presence of negatively charged functional groups on their surface.

TABLE 5

Exemplary Letrozole-loaded nanoparticle data on zeta potential

| Type | Sample ID | Zeta Potential (mV) | Mobility (μ/s)/ (V/cm) | RMS Residual |
|---|---|---|---|---|
| PALS | Letrozole-loaded NPs 001 - 5 | −8.92 | −0.70 | 1.26E−02 |
| PALS | Letrozole-loaded NPs 001 - 4 | −8.84 | −0.69 | 1.22E−02 |
| PALS | Letrozole-loaded NPs 001 - 3 | −8.73 | −0.68 | 1.22E−02 |
| PALS | Letrozole-loaded NPs 001 - 2 | −9.35 | −0.73 | 1.29E−02 |
| PALS | Letrozole-loaded NPs 001 - 1 | −9.88 | −0.77 | 1.24E−02 |
| | Mean: | −9.14 | −0.71 | 1.24E−02 |
| | Std Err: | 0.21 | 0.02 | 1.29E−04 |
| | Std Dev: | 0.47 | 0.04 | 2.88E−04 |

BSA Coating of Letrozole Nanoparticles

A solution of Letrozole-loaded nanoparticles (LTZ-loaded NPs) was prepared by dissolving 15.2 mg (±0.1) of nanoparticles in 25 mL distilled water. 100 μL of 1% BSA solution was added to 1 mL of the Letrozole-loaded nanoparticles solution. The solution then was incubated for 1 hr at 60° C. with shaking 350 rpm. The sample was then collected and dried using rotary evaporator, weighed, labeled and stored at 4° C.

The above procedure was repeated with void nanoparticles to obtain BSA-coated nanoparticles.

Purification Method of BSA-Coated Nanoparticles (Void and Drug-Loaded Nanoparticles)

The obtained white solid of letrozole-loaded nanoparticles was purified by dialysis. 100 μm membrane was placed on each side of 1,000 μL double sided reservoir and was filled with 1 mL of the solution of Letrozole-loaded nanoparticles and was placed in 250 mL of 0.06 M PBS with stirring. The PBS solution was changed every three hours three times.

The procedure was repeated with void nanoparticles to purify BSA-coated void nanoparticles. Data of exemplary void nanoparticles are exhibited in Table 6 and Table 7.

TABLE 6

Exemplary void and BSA-coated nanoparticle data

| Type | Sample ID | Eff. Diam. (nm) | Poly-dispersity | Baseline Index |
|---|---|---|---|---|
| DLS | BSA-coated void NPs 002 - 5 | 273.56 | 0.29 | 0.00 |
| DLS | BSA-coated void NPs 002 - 4 | 297.40 | 0.30 | 0.00 |
| DLS | BSA-coated void NPs 002 - 3 | 310.54 | 0.32 | 0.00 |
| DLS | BSA-coated void NPs 002 - 2 | 290.71 | 0.33 | 0.00 |
| DLS | BSA-coated void NPs 002 - 1 | 291.46 | 0.30 | 0.00 |
| | Mean: | 292.74 | 0.31 | 0.00 |
| | Std Err: | 5.97 | 0.01 | 0.00 |
| | Std Dev: | 13.34 | 0.02 | 0.00 |

TABLE 7

Exemplary Letrozole-loaded and BSA-coated nanoparticle data

| Type | Sample ID | Eff. Diam. (nm) | Poly-dispersity | Baseline Index |
|---|---|---|---|---|
| DLS | LTZ-loaded BSA-coated - 5 | 138.98 | 0.36 | 4.81 |
| DLS | LTZ-loaded BSA-coated - 4 | 151.35 | 0.35 | 8.33 |
| DLS | LTZ-loaded BSA-coated - 3 | 157.09 | 0.35 | 7.40 |
| DLS | LTZ-loaded BSA-coated - 2 | 165.61 | 0.36 | 6.46 |
| | Mean: | 153.26 | 0.35 | 6.75 |
| | Std Err: | 5.59 | 0.00 | 0.75 |
| | Std Dev: | 11.18 | 0.01 | 1.50 |

Particle Size and Size Distribution Measurement

The particle size and the size distribution were measured by dynamic light scattering (DLS). The mean diameter of the PLA-PEG-PLA NPs varied depending on the percentage of the emulsifier PVA used. It was observed that the mean particle size was directly related to the concentration of PVA used in the formula. For instance, the results presented in Table 8 show a direct correlation between the particle size and the percentage of PVA used.

TABLE 8

Effect of varying the concentration of the emulsifying agent PVA on the particle size and on the polydispersity of LTZ-loaded PLA-PEG-PLA NPs

| Formulation | % PVA | Particle Size (nm) | PDI |
|---|---|---|---|
| LTZ-Loaded NPs | 3 | 188.75 | 0.135 |
| LTZ-Loaded NPs | 2 | 145.43 | 0.189 |
| LTZ-Loaded NPs | 1 | 119.13 | 0.224 |
| LTZ-Loaded NPs | 0.5 | 107.59 | 0.246 |

Formulations tested in this work were within the size range of 120-200 nm, and showed a relatively homogeneous size distribution as revealed by polydispersity index values. In order to avoid elimination of NPs in spleen sinusoids and liver fenestrae and to effectively deliver the drug to the targeted tumor tissue, the size of loaded nanoparticles may not exceed 200 nm and may not be 6 nm or smaller to avoid rapid elimination from blood stream. As a result, this work provides a suitable method to control and tailor the size of NPs. FIG. 19 shows the variation of PVA concentrations and its effect on particle size.

Coupling of Anti-Her2 to Letrozole PLA-PEG-PLA Nanoparticles

50 μL of anti-Her2 (antibody) solution was incubated with 200 μL Letrozole PLA-PEG-PLA nanoparticles (6.45×10⁻⁴) for one hour in at 40° C. Afterward, the solution was dialyzed to remove excess anti-Her2, using a single sided dialysis chamber and a nitrocellulose membrane cut off 300 kDa. The sample has been dialyzed against 200 ml of PBS buffer, and the buffer has been discarded and changed three times every 2 hours. The final dialyzed sample has been analyzed using dynamic light scattering to measure the particle size of anti-Her2 Letrozole-loaded PLA-PEG-PLA nanoparticles.

Therapeutic Effect of LTZ-Loaded PLA-PEG-PLA NPs on Breast Cancer Cells (MCF-7)

The LTZ-loaded NPs were incubated with MCF-7 (estrogen receptor positive breast cancer cell line) for 72 hours. The cytotoxic effect of the LTZ nanoformula on the cell lines was studied by looking at the levels of gene expression of antiapoptotic genes, MAPK3 and c-MYC. LTZ-loaded NPs caused a down regulation in the expression of these two genes, suggesting that the LTZ-loaded NPs asserted the same effect as the free drug on breast cancer cell.

RNA Isolation

The RNA was isolated using a PureLink® RNA mini kit (Ambion-Life Technologies, Carlsbad, Calif.) following the manufacturer's instructions. Purity of isolated RNA was determined by measuring ratio of the optical density of the samples at 260 and 280 nm using NanoDrop™ 8000 spectrophotometer.

cDNA Synthesis

Complementary DNA strands were synthesized using a high-capacity cDNA reverse transcription kit (Applied Biosystems™) according to the manufacturer's instructions. Aliquots containing 1 μg of total RNA were used from each sample.

Gene Expression Profiling and Data Analysis

Real-time PCR for the anti-apoptotic genes, MAPK3 and c-MYC, was performed to ensure the delivery of the drug by the NPs system, compared with the free drug formula of Letrozole. Applied Biosystems 7900HT fast real-time PCR System and TaqMan® Gene Expression master mix (ThermoFisherScientific, Foster City, Calif.) was used, then the gene expression were quantitated using the delta-delta CT (AAP) method and further re-calculated manually. Changes in gene expression were illustrated as a fold increase or decrease. The data were normalized, across all plates, to the housekeeping gene: glyceraldehydes-3-phosphate dehydrogenase (GAPDH). Pre-designed primers MAPK3 (Hs00385075_m1), c-MYC (Hs00153408_m1) and GAPDH (Hs02786624_g1) were commercially obtained from Applied Biosystems, Foster City, Calif.

Effect of Letrazole Treatment on MCF-7 for 72 Hours

The MCF-7 cells were incubated with the following samples for 72 hours in separate wells: LTZ 0.5 nM, NP (nanoparticle) loaded with LTZ 0.5 nM, LTZ 1 nM, NP loaded with LTZ 1 nM, LTZ 2 nM, and NP loaded with LTZ 2 nM. The gene expression results are shown in FIGS. 20 and 21. In FIG. 20, each bar represents the expression of MAPK3 gene in the presence of each sample. In FIG. 21, each bar represents the expression of c-MYC gene in the presence of each sample.

Method of Drug Release Study

Known amounts of Letrozole PLA-PEG-PLA nanoparticles were dispersed by a bath sonicator (Branson 3800) for 20 min with the release media (1.0 mL of phosphate buffer pH 7.2). An amount equivalent to 690 mcg of the nanoparticles in 1.0 ml of release media (1.2% sodium lauryl sulfate (SLS) in 7.2 phosphate buffer) was placed inside sealed cellulose dialysis tubing with cutoff of 12,000-14,000 Da (Carolina, N.C., US). The dialysis tubing was placed in a screw cap bottle with 19.0 ml release media and kept in a shaking water bath (GFL 1083) at 37° C. and medium speed. At different time intervals, aliquots of 3.0 ml were withdrawn and immediately restored with the same volume of fresh release media. The amounts of LTZ released were assessed by double beam UV Spectrophotometer (Thermo-Evolution UV 60S, Thermo Scientific), which was set up at 310 nm for Letrozole versus a calibration curve prepared in the same buffer. FIG. 2 depicts the release rate of the drug from the nanoparticle.

The features of the presently disclosed nanoparticle include a stable nanoparticle employing a PLA-PEG-PLA triblock copolymer for the delivery of Letrozole. The PLA-PEG-PLA nanoparticles are biocompatible and biodegradable to contain the therapeutic. Further, the sustained release of Letrozole over 72 hours makes this prototype different than previously reported nanoparticles. The nanoparticle represents a first line breast cancer treatment that can be given to a patient twice weekly compared with the available oral tablet currently prescribed once daily.

The invention claimed is:

1. A method for delivering letrozole to cancer cells, comprising:
   administering a treatment composition comprising a carrier and a plurality of pharmaceutical nanoparticles to a patient to thereby deliver the letrozole to the cancer cells;
   wherein the pharmaceutical nanoparticles having an interior space and a membrane surrounding the interior space,
   wherein the interior space contains letrozole that is encapsulated by the membrane, and the membrane comprises;
   a polylactide-block-poly(ethylene glycol)-block-polylactide block (PLA-PEG-PLA) copolymer wherein a number average molecular weight range of the PEG block is 800 Da to 3 kDa and a number average molecular weight range of each of the PLA block is from 1 kDa to 5 kDa,
   a polyvinyl alcohol polymer,
   bovine serum albumin in contact with the outer surface of the membrane, and
   anti-Her2 antibody attached to the outer surface of the membrane.

2. The method of claim 1, wherein said pharmaceutical nanoparticles provide sustained release of letrozole over a period of 72 hours.

3. The method of claim 1, wherein the pharmaceutical nanoparticles comprise 60 to 95 weight percent of the polylactide-block-poly(ethylene glycol)-block-polylactide block (PLA-PEG-PLA) copolymer and 0.5 to 5 weight percent of polyvinyl alcohol polymer relative to the total weight of the pharmaceutical nanoparticles.

4. The method of claim 1, wherein the bovine serum albumin is 0.5 to 8 weight percent relative to the total weight of the pharmaceutical nanoparticles.

5. The method of claim 1, wherein the pharmaceutical nanoparticles have an average diameter of 300 nm to 370 nm.

6. The method of claim 1, wherein a rate of release of the letrozole is a cumulative percent of 25% to 75% in 24 hours to 96 hours.

7. The method of claim 1, wherein the anti-Her2 antibody is bound to the membrane via a biotin-avidin complex.

8. The method of claim 7, wherein the anti-Her2 antibody is sourced from a rabbit.

9. The method of claim 1, wherein the pharmaceutical nanoparticles have an average diameter of from 310 nm to 350 nm.

10. The method of claim 1, wherein the anti-Her2 antibody is conjugated to the membrane.

11. The method of claim 1, wherein the letrozole is 0.5 to 10 weight percent relative to the total weight of the pharmaceutical nanoparticles.

12. The method of claim 1, wherein the pharmaceutical nanoparticles have an internal volume of from 1 picoliter to 1 nanoliter.

13. The method of claim 1, wherein the pharmaceutical nanoparticles have a zeta potential of −7 mV to −20 mV.

14. The method of claim 1, wherein the membrane further comprises a diblock copolymer.

15. The method of claim 14, wherein a weight percent of the diblock copolymer relative to the total weight of the pharmaceutical nanoparticles is 0.01% to 0.1%.

16. The method of claim 14, wherein the diblock copolymer comprises one hydrophobic block polymer and one hydrophilic block polymer.

17. The method of claim 16, wherein the diblock copolymer comprises at least one hydrophobic polymer block selected from the group consisting of polycaprolactone (PCL), polyvalerolactone (PVL), poly(lactide-co-glycolide) (PLGA), polylactic acid (PLA), polybutyrolactone (PBL), polyglycolide, and polypropiolactone (PPL), and at least one hydrophilic polymer block selected from the group consisting of polyethylene glycol (PEG), hyaluronic acid (HA), and poly-γ-glutamic acid (PGA).

18. The method of claim 16, wherein a number average molecular weight range of the hydrophobic block polymer and the hydrophilic block polymer is from 800 Da to 5 kDa.

19. The method of claim 1, wherein the membrane is prepared by a double emulsion method comprising mixing a first emulsion with a second emulsion, wherein the first emulsion and the second emulsion comprise polyvinyl alcohol as an emulsifying agent.

* * * * *

UNITED STATES PATENT AND TRADEMARK OFFICE
CERTIFICATE OF CORRECTION

PATENT NO. : 10,709,795 B2  
APPLICATION NO. : 16/412047  
DATED : July 14, 2020  
INVENTOR(S) : Salam Massadeh et al.

Page 1 of 1

It is certified that error appears in the above-identified patent and that said Letters Patent is hereby corrected as shown below:

On the Title Page

Item (73), the first Assignee's information is incorrect. Item (73) should read:
--(73) Assignees:
    National Guard Health Affairs, Riyadh (SA);
    King Saud bin Abdulaziz University for Health Sciences, Riyadh (SA);
    King Abdullah International Medical Research Center, Riyadh (SA)--

Signed and Sealed this
Twenty-fifth Day of August, 2020

Andrei Iancu
*Director of the United States Patent and Trademark Office*